US007939079B2

(12) United States Patent
Baele et al.

(10) Patent No.: US 7,939,079 B2
(45) Date of Patent: May 10, 2011

(54) HELICOBACTER SPECIES AND CULTIVATION THEREOF

(75) Inventors: Margo Baele, Gent (BE); Freddy Haesebrouck, Knokke-Heist (BE)

(73) Assignee: Universiteit Gent, Gent (BE)

( * ) Notice: Subject to any disclaimer, the term of this patent is extended or adjusted under 35 U.S.C. 154(b) by 0 days.

(21) Appl. No.: 12/463,300

(22) Filed: May 8, 2009

(65) Prior Publication Data

US 2009/0285856 A1      Nov. 19, 2009

Related U.S. Application Data

(63) Continuation-in-part of application No. PCT/EP2007/009855, filed on Nov. 14, 2007.

(60) Provisional application No. 60/865,723, filed on Nov. 14, 2006, provisional application No. 61/059,401, filed on Jun. 6, 2008.

(51) Int. Cl.
 *A61K 39/00* (2006.01)
 *A61K 39/02* (2006.01)
 *A61K 38/00* (2006.01)
 *C12P 1/00* (2006.01)

(52) U.S. Cl. .................. 424/184.1; 424/234.1; 435/41; 530/300

(58) Field of Classification Search .................. None
 See application file for complete search history.

(56) References Cited

U.S. PATENT DOCUMENTS

| 6,368,847 B1 | 4/2002 | Line et al. |
| 2001/0055787 A1 | 12/2001 | Heifets et al. |

FOREIGN PATENT DOCUMENTS

| EP | 0 540 897 | 8/1999 |
| EP | 1 035 219 | 9/2000 |
| WO | WO 97/13527 | 4/1997 |
| WO | WO 00/75285 | 12/2000 |
| WO | WO 2006/091721 | 8/2006 |
| WO | WO 2006/133879 | 12/2006 |

OTHER PUBLICATIONS

Hellemans et al (Vaccine, 24, 2006, 2469-2476, available online Jan. 4, 2006).*
O'Rourke et al (International Journal of Systematic and Evolutionary Microbiology, 2004, 54, 2203-2211).*
Annex to the Response to Written Opinion of the International Preliminary Examining Authority for PCT/EP2007/009855, dated Sep. 15, 2008.
Andersen et al., "Characterization of a culturable '*Gastrospirillum hominis*' (*Helicobacter heilmannii*) strain isolated from human gastric mucosa," *Journal of Clinical Microbiology* 37: 1069-1076 (1999).
Baele et al., "Isolation and characterization of *Helicobacter suis* sp. nov. from pig stomachs," *Zoonoses Public Health* 54: Abstract O018 (2007).
Baele et al., "*Helicobacter baculiformis* sp. nov., isolated from feline stomach mucosa," *International Journal of Systematic and Evolutionary Microbiology* 58: 357-364 (2008).
Belgian Coordinated Collections of Microorganisms Deposit Accession No. LMG P-24758 (HS1), received and accepted Jul. 20, 2008.
De Groote et al., "'*Candidatus* Helicobacter suis', a gastric helicobacter from pigs, and its phylogenetic relatedness to other gastrospirilla," *International Journal of Systematic Bacteriology* 49: 1769-1777 (1999).
De Groote et al., "Detection of '*Candidatus* Helicobacter suis' in gastric samples of pigs by PCR: comparison with other invasive diagnostic techniques," *Journal of Clinical Microbiology* 38: 1131-1135 (2000).
Dieterich et al., "Urease-based mucosal immunization against *Helicobacter heilmannii* infection induces corpus atrophy in mice," *Infection and Immunity* 67: 6206-6209 (1999).
Hellemans et al., "Evaluation of antibiotic treatment against '*Candidatus* Helicobacter suis' in a mouse model," *Antimicrobial Agents and Chemotherapy* 49: 4530-4535 (2005).
Hellemans et al., "Protective immunization against '*Candidatus* Helicobacter suis' with heterologous antigens of *H. pylori* and *H. felis*," *Vaccine* 24: 2469-2476 (2006).
International Preliminary Report on Patentability for PCT/EP2007/009855, mailed Mar. 3, 2009.
International Search Report for PCT/EP2007/009855, mailed Apr. 29, 2008.
O'Rourke et al., "Description of '*Candidatus* Helicobacter heilmannii' based on DNA sequence analysis of 16S rRNA and urease genes," *International Journal of Systematic and Evolutionary Microbiology* 54: 2203-2211 (2004).
Response to Written Opinion of the International Preliminary Examining Authority for PCT/EP2007/009855, dated Sep. 15, 2008.
Solnick et al., "Emergence of diverse *Helicobacter* species in the pathogenesis of gastric and enterohepatic diseases," *Clinical Microbiology Reviews* 14: 59-97 (2001).
Van den Bulck et al., "*Helicobacter cynogastricus* sp. nov., isolated from the canine gastric mucosa," *International Journal of Systematic and Evolutionary Microbiology* 56: 1559-1564 (2006).
Written Opinion of the International Searching Authority for PCT/EP2007/009855, received Apr. 28, 2008.
Written Opinion of the International Preliminary Examining Authority for PCT/EP2007/009855, mailed Nov. 7, 2008.
Communication from the Examining Division of the European Patent Office for Application No. EP 07819811.6, dated Mar. 31, 2010.
Baele et al., "Isolation and Characterization of *Helicobacter suis* sp. nov. from Pig Stomachs," *Int. J. Syst. Evol. Microbiol*. 58:1350-1358 (2008).
GenBank Accession No. AF127028, dated Nov. 17, 1999.
Reply to Official Communication Issued in European Patent Application EP-A-2 087 095, dated Jul. 16, 2010.

* cited by examiner

*Primary Examiner* — Vanessa L. Ford
(74) *Attorney, Agent, or Firm* — Clark & Elbing LLP

(57) ABSTRACT

The present invention relates to the isolation and cultivation of "Candidatus *Helicobacter suis*" and isolates of "Candidatus *Helicobacter suis*" obtainable by these methods. The present invention further relates to the use of these bacteria for the manufacture of antigen preparations and vaccines.

3 Claims, No Drawings

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: 16S rRNA consensus primer Alphabeta-NOT

<400> SEQUENCE: 1
tcaaactagg accgagtc                                                 18

<210> SEQ ID NO 2
<211> LENGTH: 20
<212> TYPE: DNA
<213> ORGANISM: Artificial Sequence
<220> FEATURE:
<223> OTHER INFORMATION: 16S rRNA Consensus primer omega MB

<400> SEQUENCE: 2
taccttgtta cttcaccccca                                              20

<210> SEQ ID NO 3
<211> LENGTH: 18
<212> TYPE: DNA
<213> ORGANISM: Artificial Sequence
<220> FEATURE:
<223> OTHER INFORMATION: 16S rRNA sequence primer pD

<400> SEQUENCE: 3
cagcagccgc ggtaatac                                                 18

<210> SEQ ID NO 4
<211> LENGTH: 20
<212> TYPE: DNA
<213> ORGANISM: Artificial Sequence
<220> FEATURE:
<223> OTHER INFORMATION: 16S rRNA sequence primer gamma asterisk

<400> SEQUENCE: 4
ctcctacggg aggcagcagt                                               20

<210> SEQ ID NO 5
<211> LENGTH: 20
<212> TYPE: DNA
<213> ORGANISM: Artificial Sequence
<220> FEATURE:
<223> OTHER INFORMATION: 16S rRNA sequence primer 3

<400> SEQUENCE: 5
gttgcgctcg ttgcgggact                                               20

<210> SEQ ID NO 6
<211> LENGTH: 19
<212> TYPE: DNA
<213> ORGANISM: Artificial Sequence
<220> FEATURE:
<223> OTHER INFORMATION: 16S rRNA sequence primer O asterisk

<400> SEQUENCE: 6
aactcaaagg aattgacgg                                                19

<210> SEQ ID NO 7
<211> LENGTH: 1421
<212> TYPE: DNA

<213> ORGANISM: Candidatus Helicobacter suis
<220> FEATURE:
<221> NAME/KEY: misc_feature
<222> LOCATION: (1)..(1421)
<223> OTHER INFORMATION: 16S ribosomal RNA gene, partial sequence

<400> SEQUENCE: 7

| | | |
|---|---|---|
| tgcaagtcga acgatgaagc ctagcttgct aggttgatta gtggcgcacg ggtgagtaat | 60 |
| gcatagatga catgcccttt agtttggaat agccactaga aatggtgatt ataccaaat | 120 |
| actaccttac gagggaaaga tttatcgcta aaggattggt ctatgtccta tcagcttgtt | 180 |
| ggtgaggtaa aggctcacca aggctatgac gggtatccgg cctgagaggg tgagcggaca | 240 |
| cactggaact gagacacggt ccagactcct acgggaggca gcagtaggga atattgctca | 300 |
| atggggaaa ccctgaagca gcaacgccgc gtggaggatg aaggttttag gatcgtaaac | 360 |
| tcctttgtt agagaagata atgacggtat ctaacgaata agcaccggct aactccgtgc | 420 |
| cagcagccgc ggtaatacgg agggtgcaag cgttactcgg aatcactggg cgtaaagagt | 480 |
| gcgtaggcgg gaggacaagt caggtgtgaa atcctatggc ttaaccatag aactgcattt | 540 |
| gaaactatcc ttctggagtg tgggagaggt aggtggaatt cttggtgtag gggtaaaatc | 600 |
| cgtagagatc aagaggaata ctcattgcga aggcgacctg ctggaacatc actgacgctg | 660 |
| attgcacgaa agcgtgggga gcaaacagga ttagataccc tggtagtcca cgccctaaac | 720 |
| gatggatgct agttgttggg aggctttgtc tttccagtaa tgcagctaac gccttaagca | 780 |
| tcccgcctgg ggagtacggt cgcaagatta aaactcaaag gaatagacgg gacccgcac | 840 |
| aagcggtgga gcatgtggtt taattcgaag ttacacgaag aaccttacct aggcttgaca | 900 |
| ttgaaggaat tccctagaaa taggggagtg tctagcttgc tagaccctga aaacaggtgc | 960 |
| tgcacggctg tcgtcagctc gtgtcgtgag atgttgggtt aagtcccgca acgagcgcaa | 1020 |
| cccttttct tagttgctaa caggttatgc tgcgcactct aagaagactg cctgcgtaag | 1080 |
| caggaggaag gtgaggacga cgtcaagtca tcatggccct tacgcctagg ctacacacg | 1140 |
| tgctacaatg gggtgcacaa agagatgcaa agccgcgagg cagagctaat ctataaaaca | 1200 |
| cctcctagtt cggattgcag gctgcaactc gcctgcatga agctggaatc gctagtaatc | 1260 |
| gcaaatcagc tatgttgcgg tgaatacgtt cccgggtctt gtactcaccg cccgtcacac | 1320 |
| catgggagtt gtgtttgcct taagtcagga tgctaaagca gctactgccc acggcacaca | 1380 |
| cagcgactgg ggtgaagtcg taacaaggta acccgggcgg c | 1421 |

<210> SEQ ID NO 8
<211> LENGTH: 1221
<212> TYPE: DNA
<213> ORGANISM: Candidatus Helicobacter Heilmannii
<220> FEATURE:
<221> NAME/KEY: misc_feature
<223> OTHER INFORMATION: Strain P4 urease UreA (ureA) and urease UreB
      (ureB)

<400> SEQUENCE: 8

| | | |
|---|---|---|
| tgcaagaagg taggaatttt gcttaaagca gatgatgtaa tgcccggtgt tgcccatatg | 60 |
| attcatgaag tgggcattga agcaaatttt cctgatggaa ctaaacttgt taccatccac | 120 |
| actcccgtag aagctggaag cgacaaacac caccccgggg aagtgatctt gaaaaacgaa | 180 |
| gacatcactt taaatgctgg caaagaagct atcgaactca agtaaaaaaa cacaggcgat | 240 |
| cgccctgtac aagtaggctc tcacttccat ttctttgaag ttaacaaact gttagactttt | 300 |
| gatcgcgaaa aagcttatgg caaacgactt gacatcgcct ctggtacagc tgtgcgcttt | 360 |

```
gaacctggcg aagaaaaaac cgtgcatttg attgatgtag gcggcaataa acgcatctat    420
ggctttaatg ctttggtaga tagacaagcc gatcacgatg gcaaaaaact agctctcaaa    480
cgcgcaaaag caaacattt tggcactgtt aattgcggtt gcgatcacga aaataaataa    540
ggaaaggaca agcgatgaaa aaatctcta ggaaagaata tgtttctatg tatggcccca    600
ctacaggcga taaagtcaga ctaggcgata cagatctgat tttagaagta gagcatgact    660
gcaccactta tggcgaagaa atcaaatttg ggggcgggaa aactatccgc gatgggatgg    720
gccaaaccaa tagccccagc agccatgagt tagatttagt gattactaac gccctaattg    780
tagactacac cgggatttac aaagccgaca ttggcattaa agatggcaag atccatggca    840
ttggtaaagc cggcaataaa gacattcaag acggcgtttg caaccgcctt tgtgtaggtc    900
ctgctacaga agcactagct ggtgaaggtt taattgttac agctggcggg attgataccc    960
acattcactt tatttctcca caacaaatcc ccaccgcttt tgctagcggc attacaacca   1020
tgcttggagg cggaacaggc cctgctgatg gtactaatgc gacaactatc actccaggcc   1080
gctggaattt aaaagaaatg ctccgcgcct ctgaagaata cgccatgaat ttaggctaca   1140
tgggtaaagg taatgtttct tatgaacctt ctttggttga acaacttgaa gctggggcta   1200
ttggccttaa aatccacgaa g                                             1221

<210> SEQ ID NO 9
<211> LENGTH: 179
<212> TYPE: PRT
<213> ORGANISM: Candidatus Helicobacter suis

<400> SEQUENCE: 9

Cys Lys Lys Val Gly Ile Leu Leu Lys Ala Asp Asp Val Met Pro Gly
1               5                   10                  15

Val Ala His Met Ile His Glu Val Gly Ile Glu Ala Asn Phe Pro Asp
            20                  25                  30

Gly Thr Lys Leu Val Thr Ile His Thr Pro Val Glu Ala Gly Ser Asp
        35                  40                  45

Lys His His Pro Gly Glu Val Ile Leu Lys Asn Glu Asp Ile Thr Leu
    50                  55                  60

Asn Ala Gly Lys Glu Ala Ile Glu Leu Lys Val Lys Asn Thr Gly Asp
65                  70                  75                  80

Arg Pro Val Gln Val Gly Ser His Phe His Phe Glu Val Asn Lys
                85                  90                  95

Leu Leu Asp Phe Asp Arg Glu Lys Ala Tyr Gly Lys Arg Leu Asp Ile
            100                 105                 110

Ala Ser Gly Thr Ala Val Arg Phe Glu Pro Gly Glu Glu Lys Thr Val
        115                 120                 125

His Leu Ile Asp Val Gly Gly Asn Lys Arg Ile Tyr Gly Phe Asn Ala
    130                 135                 140

Leu Val Asp Arg Gln Ala Asp His Asp Gly Lys Lys Leu Ala Leu Lys
145                 150                 155                 160

Arg Ala Lys Ala Lys His Phe Gly Thr Val Asn Cys Gly Cys Asp His
                165                 170                 175

Glu Asn Lys

<210> SEQ ID NO 10
<211> LENGTH: 222
<212> TYPE: PRT
<213> ORGANISM: Candidatus Helicobacter suis

<400> SEQUENCE: 10
```

Met Lys Lys Ile Ser Arg Lys Glu Tyr Val Ser Met Tyr Gly Pro Thr
1               5                   10                  15

Thr Gly Asp Lys Val Arg Leu Gly Asp Thr Asp Leu Ile Leu Glu Val
            20                  25                  30

Glu His Asp Cys Thr Thr Tyr Gly Glu Ile Lys Phe Gly Gly Gly
            35                  40                  45

Lys Thr Ile Arg Asp Gly Met Gly Gln Thr Asn Ser Pro Ser Ser His
        50                  55                  60

Glu Leu Asp Leu Val Ile Thr Asn Ala Leu Ile Val Asp Tyr Thr Gly
65                  70                  75                  80

Ile Tyr Lys Ala Asp Ile Gly Ile Lys Asp Gly Lys Ile His Gly Ile
                85                  90                  95

Gly Lys Ala Gly Asn Lys Asp Ile Gln Asp Gly Val Cys Asn Arg Leu
            100                 105                 110

Cys Val Gly Pro Ala Thr Glu Ala Leu Ala Gly Glu Gly Leu Ile Val
            115                 120                 125

Thr Ala Gly Gly Ile Asp Thr His Ile His Phe Ile Ser Pro Gln Gln
130                 135                 140

Ile Pro Thr Ala Phe Ala Ser Gly Ile Thr Thr Met Leu Gly Gly Gly
145                 150                 155                 160

Thr Gly Pro Ala Asp Gly Thr Asn Ala Thr Thr Ile Thr Pro Gly Arg
                165                 170                 175

Trp Asn Leu Lys Glu Met Leu Arg Ala Ser Glu Glu Tyr Ala Met Asn
                180                 185                 190

Leu Gly Tyr Met Gly Lys Gly Asn Val Ser Tyr Glu Pro Ser Leu Val
            195                 200                 205

Glu Gln Leu Glu Ala Gly Ala Ile Gly Leu Lys Ile His Glu
210                 215                 220

<210> SEQ ID NO 11
<211> LENGTH: 160
<212> TYPE: PRT
<213> ORGANISM: Candidatus Helicobacter Heilmannii
<220> FEATURE:
<221> NAME/KEY: MISC_FEATURE
<223> OTHER INFORMATION: Strain P4 urease UreA

<400> SEQUENCE: 11

Cys Lys Lys Val Gly Ile Leu Leu Lys Ala Asp Asp Val Met Pro Gly
1               5                   10                  15

Val Ala His Met Ile His Glu Val Gly Ile Glu Ala Asn Phe Pro Asp
            20                  25                  30

Gly Thr Lys Leu Val Thr Ile His Thr Pro Val Glu Ala Gly Ser Asp
        35                  40                  45

Lys His His Pro Gly Glu Val Ile Leu Lys Asn Glu Asp Ile Thr Leu
    50                  55                  60

Asn Ala Gly Lys Glu Ala Ile Glu Leu Lys Val Lys Asn Thr Gly Asp
65              70                  75                  80

Arg Pro Val Gln Val Gly Ser His Phe His Phe Phe Glu Val Asn Lys
                85                  90                  95

Leu Leu Asp Phe Asp Arg Glu Lys Ala Tyr Gly Lys Arg Leu Asp Ile
            100                 105                 110

Ala Ser Gly Thr Ala Val Arg Phe Glu Pro Gly Glu Glu Lys Thr Val
        115                 120                 125

His Leu Ile Asp Val Gly Gly Asn Lys Arg Ile Tyr Gly Phe Asn Ala
    130                 135                 140

-continued

```
Leu Val Asp Arg Gln Ala Asp His Asp Gly Lys Lys Leu Ala Leu Lys
145                 150                 155                 160

<210> SEQ ID NO 12
<211> LENGTH: 222
<212> TYPE: PRT
<213> ORGANISM: Candidatus Helicobacter Heilmannii
<220> FEATURE:
<221> NAME/KEY: MISC_FEATURE
<223> OTHER INFORMATION: Strain P4 urease UreB

<400> SEQUENCE: 12

Met Lys Lys Ile Ser Arg Lys Glu Tyr Val Ser Met Tyr Gly Pro Thr
1               5                   10                  15

Thr Gly Asp Lys Val Arg Leu Gly Asp Thr Asp Leu Ile Leu Glu Val
                20                  25                  30

Glu His Asp Cys Thr Thr Tyr Gly Glu Glu Ile Leu Phe Gly Gly Gly
                35                  40                  45

Lys Thr Ile Arg Asp Gly Met Gly Gln Thr Asn Ser Pro Ser Ser His
        50                  55                  60

Glu Leu Asp Leu Val Ile Thr Asn Ala Leu Ile Val Asp Tyr Thr Gly
65                  70                  75                  80

Ile Tyr Lys Ala Asp Ile Gly Ile Lys Asp Gly Lys Ile His Gly Ile
                85                  90                  95

Gly Lys Ala Gly Asn Lys Asp Ile Gln Asp Gly Val Cys Asn Arg Leu
                100                 105                 110

Cys Val Gly Pro Ala Thr Glu Ala Leu Ala Gly Glu Gly Leu Ile Val
                115                 120                 125

Thr Ala Gly Gly Ile Asp Thr His Ile His Phe Ile Ser Pro Gln Gln
        130                 135                 140

Ile Pro Thr Ala Phe Ala Ser Gly Ile Thr Thr Met Leu Gly Gly Gly
145                 150                 155                 160

Thr Gly Pro Ala Asp Gly Thr Asn Ala Thr Thr Ile Thr Pro Gly Arg
                165                 170                 175

Trp Asn Leu Lys Glu Met Leu Arg Ala Ser Glu Glu Tyr Ala Met Asn
                180                 185                 190

Leu Gly Tyr Met Gly Lys Gly Asn Val Ser Tyr Glu Pro Ser Leu Val
                195                 200                 205

Glu Gln Leu Glu Ala Gly Ala Ile Gly Leu Lys Ile His Glu
        210                 215                 220
```

HELICOBACTER SPECIES AND CULTIVATION THEREOF

CROSS REFERENCE TO RELATED APPLICATIONS

This application is a continuation-in-part of International Application No. PCT/EP2007/009855, filed on Nov. 14, 2007, which was published in English under PCT Article 21(2), and which claims the benefit of U.S. Provisional Application Ser. No. 60/865,723, filed on Nov. 14, 2006, the disclosures of which are incorporated by reference in their entirety. This application also claims the benefit of U.S. Provisional Application Ser. No. 61/059,401, filed on Jun. 6, 2008, the disclosure of which is incorporated by reference in its entirety.

FIELD OF THE INVENTION

The present invention relates to the in vitro isolation and/or cultivation of *Helicobacter* species, more particularly "Candidatus *Helicobacter suis*". The invention further relates to the preparation of antigens and vaccines from the isolated cultures of "Candidatus *Helicobacter suis*".

BACKGROUND

*Helicobacter pylori* infections in humans are a major cause of gastric and duodenal ulceration as well as gastric cancer. *H. pylori* is not the only *Helicobacter* species capable of colonizing the human gastric mucosa. "*Helicobacter heilmannii*" (proposed name) has been found in approximately 0.96% of gastric biopsies in humans (Heilmann & Borchard (1991) *Gut* 32, 137-140). This organism is strongly associated with gastritis but is also associated with peptic ulceration, gastric adenocarcinoma, and mucosa-associated lymphoid tissue lymphoma. Recent evidence indicates that "*H. heilmannii*" is not a single species but represents different bacterial species with similar spiral morphologies, most of which are probably of zoonotic origin. Classification into "*H. heilmannii*" type 1 and "*H. heilmannii*" type 2 was established on the basis of 16S rRNA gene sequences (Solnick et al., (1993) *J. Infect. Dis.* 168, 379-385). More than 50% of the "*H. heilmannii*" infections in humans are due to "*H. heilmannii*" type 1 (Trebesius et al. (2001) *J. Clin. Microbiol.* 39, 1510-1516.). "*H. heilmannii*" type 1 has been shown to be identical to "Candidatus *H. suis*" (O'Rourke et al. (2004) *Int. J. Syst. Evol. Microbiol.* 54, 2203-2211), a hitherto non-culturable spiral bacterium that colonizes the stomachs of more than 60% of slaughter pigs. The actual role of Candidatus *H. suis* in gastric disease in pigs is still a matter of debate, but it has been suggested that this bacterium is associated with gastric ulceration of the pars oesophagea and with chronic pyloric gastritis. Mouse inoculation was used to isolate this bacterium from infected pig stomach mucosa (Dick et al., (1989) *J. Med. Microbiol.* 29, 55-62). Hellemans et al. ((2005) *Antimicrob. Agents Chemother.* 49, 4530-4535) modified the existing in vivo mouse model of Candidatus *H. suis* infection, for evaluating the antibiotic susceptibility of this organism. In vitro cultivation of Candidatus *H. suis* has not been achieved yet.

SUMMARY OF THE INVENTION

The present invention is based on the development of cultivation systems which allow the isolation and cultivation of *Helicobacter* species, more particularly of "Candidatus *Helicobacter suis*", which had not previously been demonstrated to be sustainable as an in vitro isolate.

A first aspect of the present invention relates to the use of a cultivation system, more particularly a cultivation system comprising a solid component, i.e., a solid medium, comprising at least 7.5% blood or 10% serum, the solid medium being adjusted to a pH between 5.0 and 6.0, for the isolation of *Helicobacter* species.

In a specific embodiment, the solid component comprises nutrients for the growth of fastidious organism. Most particularly these nutrients are selected from the group consisting of *Brucella*, Mueller-Hinton or Brain Heart Infusion medium.

In further specific embodiments, the serum present in the solid component is serum in a concentration of at least 12.5%. In another specific embodiment, the blood present in the solid component is present in a concentration of at least 10%.

More specifically the invention relates to the use of the cultivation systems described above in the isolation of "Candidatus *Helicobacter suis*"

In a second aspect, the present invention provides methods for the isolation of *Helicobacter* species, more particularly "Candidatus *Helicobacter suis*", from a sample comprising the same *Helicobacter* species, which methods comprise the steps of cultivating the sample comprising *Helicobacter* species in a cultivation system comprising a cultivation medium having a pH between 5.0 and 6.0, which is supplemented with at least 10% serum or at least 7.0% blood.

In specific embodiments of these methods, the cultivation medium used comprises nutrients for the growth of fastidious bacteria. More specifically, the nutrients for the growth of fastidious bacteria are selected from the group consisting of *Brucella*, Mueller-Hinton or Brain Heart Infusion nutrients. Additionally or alternatively, in specific embodiments, the cultivation medium comprises at least one selective substance that inhibits the growth of fungi and/or Gram positive and/or Gram negative bacteria other than the *Helicobacter* species to be cultivated. In further specific embodiments, the at least one selective substance is selected from the group consisting of: vancomycin, trimethoprim lactate, polymyxin B, cefsulodin, colistin, amphotericin B, crystal violet, nystatin and nisin.

In specific embodiments of the methods of the present invention described herein, the cultivation medium comprising at least 10% serum comprises between 12.5 and 25% serum. Alternatively, the cultivation medium comprising at least 7.0% blood comprises between 7.5 and 15%, more particularly between 10 and 15% blood.

Optionally, the cultivation medium used in the methods of the present invention further comprises one or more growth factors selected from the group consisting of Vitamin B12, L-glutamine, Adenine, Guanine, p-Aminobenzoic acid, L-cystine, NAD (Coenzyme 1), Cocarboxylase, Ferric nitrate, Thiamine and Cysteine hydrochloride.

In a specific embodiment of the methods of the invention described herein, a cultivation system is used which comprises a solid and a liquid component, wherein at least the solid component comprises the cultivation medium as described above. In further embodiments, both the solid and/or liquid component comprise nutrients for the growth of fastidious bacteria. More specifically, these nutrients are selected from the group consisting of *Brucella*, Mueller-Hinton or Brain Heart Infusion nutrients.

In a further specific embodiment of the methods of the invention, the solid and/or liquid component of the cultivation systems comprise at least one selective substance that inhibits the growth of fungi and/or Gram positive and/or Gram negative bacteria other than the *Helicobacter* species to be cultured. More particularly, the at least one selective substance is selected from the group consisting of: vancomycin, trimethoprim lactate, polymyxin B, cefsulodin, colistin, amphotericin B, crystal violet, nystatin and nisin.

Further specific embodiments of the methods of the invention make use of cultivation systems comprising a solid and a liquid component, wherein the solid component comprises between 12.5 and 25% serum or between 7.5 and 15%, more particularly between 10 and 15% blood.

Further specific embodiments of the methods of the invention make use of cultivation systems comprising a solid and a liquid component as described above, wherein the solid and/or liquid component further comprises one or more growth factors selected from the group consisting of Vitamin B12, L-glutamine, Adenine, Guanine, p-Aminobenzoic acid, L-cystine, NAD (Coenzyme 1), Cocarboxylase, Ferric nitrate, Thiamine and Cysteine hydrochloride.

The methods of the present invention are particularly suited for the isolation of "Candidatus *Helicobacter suis*". Indeed, the present invention provides, for the first time, a method for obtaining a "Candidatus *Helicobacter suis*" isolate. This isolate is free from other *Helicobacter* species, from non-*Helicobacter* bacteria and from fungi.

Accordingly, a third aspect of the present invention provides isolates of *Helicobacter* species, more particularly isolates of "Candidatus *Helicobacter suis*". Such isolates, which are here demonstrated for the first time, are obtainable by the methods of the present invention. A particular embodiment of this aspect of the invention provides the deposited culture LMG P-24758 and cultures of Candidatus *Helicobacter suis* obtained therefrom.

Yet another aspect of the present invention provides methods for the cultivation of isolates of *Helicobacter* species, which methods comprise the step of applying the *Helicobacter* isolate in a cultivation system comprising a cultivation medium having a pH between 4.0 and 7.0 which is supplemented with at least 10% serum or at least 7.5% blood, and incubating the isolate therein.

In specific embodiments of the methods according to this aspect of the invention, the cultivation system used comprises a solid and a liquid component, and at least the solid component of this cultivation system comprises the above described cultivation medium.

In further specific embodiments of these methods of cultivation provided in the present invention, the solid and the liquid component comprise nutrients for the growth of fastidious bacteria.

In specific embodiments, at least the solid component of the cultivation system used in the methods of cultivation of the present invention, is buffered at a pH between 4.7 and 7.0.

Yet another aspect of the present invention provides cultivation recipients comprising a solid cultivation medium for the isolation and/or cultivation of *Helicobacter* species, the solid medium comprising: nutrients for the growth of fastidious organisms, blood in a concentration between 7.5 and 15% or serum in a concentration between 12.5 and 25%, and at least one selective substance that inhibits the growth of fungi and/or Gram positive and/or Gram negative bacteria other than the *Helicobacter* species to be cultured, which cultivation recipient is characterized in that the pH of the solid medium comprised therein is between 5.0 and 6.0. More specifically, at least one selective substance is selected from the group consisting of vancomycin, trimethoprim lactate, polymyxin B, cefsulodin, colistin, amphotericin B, crystal violet, nystatin and nisin.

In specific embodiments of the cultivation recipients of the present invention, the solid medium comprises agar.

Yet a further aspect of the present invention provides vaccines comprising an antigen preparation of a "Candidatus *Helicobacter suis*" isolate. Indeed, the present invention provides methods for producing antigen preparations of "Candidatus *Helicobacter suis*", which methods comprise the isolation and optionally cultivation of "Candidatus *Helicobacter suis*" according to the methods described above and the production of an antigen preparation from the obtained "Candidatus *Helicobacter suis*" isolate.

Additionally, the present invention provides vaccines comprising a live attenuated "Candidatus *Helicobacter suis*" isolate, and/or a whole killed "Candidatus *Helicobacter suis*" isolate and methods for preparing such vaccines which comprise the isolation and optionally cultivation methods described above.

In particular embodiments the invention provides vaccines comprising an antigen preparation of "Candidatus *Helicobacter suis*" isolate deposited as LMG P-24758.

Yet another aspect of the present invention provides methods for vaccinating an animal against a "Candidatus *Helicobacter suis*" infection, which methods comprise administering to the animal a vaccine comprising one or more of an antigen preparation from a "Candidatus *Helicobacter suis*" isolate, a live attenuated "Candidatus *Helicobacter suis*" isolate, and/or whole killed "Candidatus *Helicobacter suis*" isolate.

Similarly, the present invention envisages the use of an isolate of a *Helicobacter* species, more particularly a "Candidatus *Helicobacter suis*" isolate, which can be isolated and/or cultivated by the methods described herein, or the use of antigen preparations obtained from a "Candidatus *Helicobacter suis*" isolate, for the manufacture of a vaccine for the prevention and/or treatment of a *Helicobacter* species infection. More particularly, the use of a preparation of *Helicobacter* species, most particularly of "Candidatus *Helicobacter suis*" is envisaged for the manufacture of a vaccine for the prevention and/or treatment of a *Helicobacter* species infection, most particularly for immunization against "Candidatus *Helicobacter suis*".

In particular embodiments, the present invention relates to methods of vaccinating an animal against a "Candidatus *Helicobacter suis*" infection comprising administering to said animal a vaccine comprising one or more of:

one or more antigen preparations from the "Candidatus *Helicobacter suis*" isolate deposited as LMG P-24758, live attenuated "Candidatus *Helicobacter suis*" of the "Candidatus *Helicobacter suis*" isolate deposited as LMG P-24758, and/or whole killed "Candidatus *Helicobacter suis*" of the "Candidatus *Helicobacter suis*" isolate deposited as LMG P-24758.

DETAILED DESCRIPTION OF THE INVENTION

The present invention will be described with reference to certain embodiments but the present invention is not limited thereto but only by the claims.

The terms "Candidatus *Helicobacter suis*" (or Candidatus *H. suis* or *H. suis*) as used herein refers to a bacterium that was previously known as "*Helicobacter heilmannii*" type I (Trebesius et al. (2001) *J. Clin. Microbiol.* 39, 1510-1516). It is now accepted that "*H. heilmannii*" type 1 is identical to "Candidatus *H. suis*" (O'Rourke et al. (2004) *Int. J. Syst. Evol. Microbiol.* 54, 2203-2211; De Groote et al. (1999) *Int. J. Syst. Bacteriol.* 49, 1769-1777), a spirally shaped bacterium that colonizes the stomach of more than 60% of slaughter pigs. "Candidatus *Helicobacter suis*" is also defined at the molecular level as the *Helicobacter* species having a 16S rRNA gene sequence with Genbank Accession AF127028 [SEQ ID NO:7] (De Groote et al. (1999) cited above) and AF506788-92 (O'Rourke et al. (2004) cited above) and a urease gene sequence as depicted in Genbank Accession AF508013 [SEQ ID NO:8] and AF508014 (O'Rourke et al. (2004) *Int. J. Syst. Evol. Microbiol.* 54, 2203-2211).

The term "isolate" as used herein, is a pure, homogeneous, in vitro culture of a microorganism. It can be derived from a heterogeneous, wild population of microorganisms by in vitro cultivation thereof.

The term "cultivation recipients" as used in the context of the present invention relates to a recipient suitable for cultivating microorganisms, such as but not limited to Petri dishes, culture flasks, roller bottles and cell factories. The term "antigen preparation" as used in the context of the present invention relates to a composition comprising at least one protein or fragment thereof which provokes an immune response (hereafter referred to as "antigen") when administered to an animal.

The term "vaccine" as used herein refers to a composition such as an antigen preparation described above, for administration to an animal or human with the object of stimulating an immune response in the animal or human directed against a disease-causing organism, to protect the animal or human from illness or disease caused by that organism. Vaccines can comprise whole disease-causing organisms (killed or weakened) or parts of such organisms, or synthetic molecules corresponding to all or parts of such organisms. The term vaccine encompasses both compositions used for prophylactic use, i.e., for administration to the animal or human prior to infection, with the intent to prevent initial (and/or recurrent) infection and compositions for therapeutic use, i.e., for administration to the animal or human after infection with the intent to reduce or arrest disease progression caused by the organism.

The process of vaccinating whereby antigens from one species are used to protect against disease caused by another species is referred to as "cross-vaccination" or "heterologous vaccination".

The term "gastric material" as used herein refers to any material obtained directly or indirectly from the gastrointestinal tract from human or other animals. Such materials include, for example, gastric epithelium, gastric mucosa and digestive fluids.

The term "medium" as used herein refers to a liquid, solid or semi-solid composition suitable for the growth of microorganisms.

Concentrations are expressed as vol/vol percentages. This applies to liquid media but also to solid media, prior to their solidification (e.g., lukewarm agar broth).

The term "fastidious organisms" is used herein according to its standard meaning in bacteriology, i.e., to refer to bacteria having complex nutritional requirements [Stedmans Medical Dictionary].

A first aspect of the invention provides in vitro methods for isolating and/or cultivating *Helicobacter* species, in particular "Candidatus *Helicobacter* suis". The in vitro isolation of *H. suis* has not yet been described to date. The present invention provides methods which allow the selective growth of *Helicobacter* species, more particularly "Candidatus *Helicobacter suis*".

Selective growth conditions for "Candidatus *Helicobacter suis*" have been achieved by the combination of high concentrations of blood or serum and the provision of optimal pH conditions. The pH conditions which are beneficial for the growth of *Helicobacter* species are at the same time detrimental for a number of non-Helicobacter bacteria and fungi. By applying low pH, contamination is reduced, allowing "Candidatus *Helicobacter suis*" to expand.

In the isolation methods of the present invention, a sample comprising *Helicobacter* species is cultivated in a medium, the pH of which is adjusted to a value between about 5.0 and about 6.0. This pH adjustment can be performed by the addition of a concentrated acid to the medium nutrients, which provide sufficient buffering capacity, by the presence of amino acids which act as zwitter ions. Alternatively biocompatible buffers with a high buffering capacity around pH 5.0 to 5.5 (such as acetate or phosphate) are added to the cultivation medium. It was surprisingly found that the isolation of "Candidatus *Helicobacter* suis" at pH values between 5.0 and 6.0 resulted in spiral mobile bacteria, while outside this pH region, Candidatus *H. suis* appears as coccoid non-motile forms. As explained later in detail in the examples the effect of the pH on Candidatus *H. suis* changes to some extent with subsequent passaging. The isolation of Candidatus *H. suis* is successful at a pH between 5.0 and 6.0.

According to one embodiment, the methods of the present invention comprise the application of a sample containing *Helicobacter*, more particularly Candidatus *H. suis* to a cultivation system, which is a two component cultivation system, comprising a solid component and a liquid (or semi-liquid) component, whereby the sample is provided in the liquid component. Typically the solid component comprises agar, and the liquid component is a broth comprising at least nutrients. It has been observed that in such cultivation systems, the *Helicobacter* isolate remains in the fluid fraction and can be subcultured by transferring to another solid component. Where a two-component system is used in the isolation methods of the present invention, at least the solid component has a pH between 5.0 and 6.0.

The cultivation medium in the isolation methods of the present invention comprises high concentrations of blood (between 7.5 and 25%) or a blood component such as serum (between 12.5 and 30%). Unless otherwise indicated serum and blood concentration are volume percentages (v/v) in the medium. In particular embodiments, the concentration of serum in the medium is between 12.5 and 25% including concentrations such as 12.5, 15, 17.5, 20 and 25%. In other particular embodiments, the concentration of blood in the medium is between 7.5 and 25%, more particularly between 8 and 20%, especially between 9 and 15%, including concentrations such as 9.5, 10 and 12.5%. Where a two-component cultivation system is used, at least the solid component, but optionally also the liquid component of the cultivation system should contain the specified serum or blood concentration.

The serum present in the cultivation medium used in the context of the present invention can be either fetal, newborn or adult serum of different species of animal, such as, but not limited to cattle, horse, sheep, goat, or pig, more particularly horse serum, or a combination thereof. Typically, serum contains inter alia iron-binding proteins such as albumin and transferrin, which provide iron to *Helicobacter*. Suitable serum or blood substitutes containing such essential components thereof can also be used.

Different types of blood are suitable for the methods of the present invention such as, but not limited to cattle, horse, sheep, goat or pig blood. In particular embodiments, the concentration of blood in the medium is between 7.5 and 15% including concentrations such as 10 and 12.5% blood.

According to particular embodiments, the cultivation media used in the initial isolation methods of the present invention further comprise antimicrobial agents further ensuring the selective growth of *Helicobacter*. Such antimicrobial agents include antibacterial agents and antifungal agents, which limit or inhibit growth of non-Helicobacter bacteria or yeast potentially present in the sample. Where a two-component system is used these anti-microbial agents are present at least in the solid component, and optionally also in the fluid or semi-fluid component.

In particular embodiments, the cultivation medium of the present invention comprises one or more antibiotics inhibiting the growth of fungi and/or Gram positive and/or Gram negative bacteria different from the *Helicobacter* species to be cultured. Examples of such antibiotics are vancomycin, trimethoprim lactate, polymyxin B, cefsulodin, colistin, amphotericin B, crystal violet, nystatin and nisin. A commercially available antibiotic composition which is suitable in the methods of the present invention is, for example, Skirrow supplement (Oxoid) resulting in a final concentration in the medium of 10 mg/ml vancomycin, 5 mg/l trimethoprim lactate and 2500 IU/l polymyxin B. Other antibiotic compounds are, for example, antifungal compounds such as Amphotericin B (fungizone).

Using the isolation methods described above, isolates from Candidatus *H. suis*, i.e., cultures which can be maintained and passaged in vitro without requiring passage in a living host, have been obtained. An example of such an isolate has been deposited as LMG P-24758 (see below).

Once an isolate of *Helicobacter*, such as Candidatus *H. suis*, has been obtained, it can be further cultivated using the cultivation conditions described above for the isolation methods of the present invention. However, it has been observed that the cultivation of an isolated culture is possible at broader pH ranges, i.e., between 4.0 and 7.0. The pH is more critical in the isolation procedure as, at a pH above 6.0, the contaminants present in the freshly isolated stomach samples (other bacteria and fungi) will outgrow the *Helicobacter* present in the sample, which is detrimental to isolation. It has been observed however, that for isolates of Candidatus *H. suis* containing fewer contaminants, growth at a pH up to 7.0 is possible. Accordingly, the present invention further provides cultivation methods for isolates of *Helicobacter*, more particularly Candidatus *H. suis*, as described above, wherein the pH of the cultivation medium is between about 4.0 and about 7.0, in particular between (and including) about 4.7 and 6.0. The cultivation methods of the present invention are particularly suited for the cultivation of the isolate deposited as LMG P-24758 and isolates derived therefrom.

The antibiotics and antifungals described above are especially suitable in the isolation process wherein different bacteria and fungi are present in a sample. However, once a pure isolate is obtained the cultivation can be achieved with less or without antibiotics or antifungals in the cultivation medium.

In particular embodiments of both the isolation and/or cultivation methods of the present invention, the cultivation medium further comprises additional growth factors. A commercial mixture of growth factors is, for example, sold under the name of Vitox (Oxoid). Final concentrations of growth factors of this commercial composition in a growth medium (e.g., agar or broth) are vitamin B12 (0.5 mg/l), L-glutamine (50.0 mg/l), adenine (5.0 mg/l), guanine (0.15 mg/l), p-aminobenzoic acid (0.65 mg/l), L-cystine (5.5 mg/l), NAD Coenzyme-1 (1.25 mg/l), cocarboxylase (0.5 mg/l), ferric nitrate (0.1 mg/l), thiamine (0.015 mg/l) and Cysteine hydrochloride (130.0 mg/l). Where a two-component system is used, the growth factors can be present in either the solid component or the liquid component or both. According to a particular embodiment, the growth factors are added to the solid component.

Typically, the medium used in the isolation and/or cultivation methods of the present invention contains nutrients for the growth of fastidious organisms. These nutrients are typically provided by the addition of media such as, but not limited to, *Brucella* medium, Mueller-Hinton medium, bovine and porcine Brain Heart Infusion and equivalent media, such as, but not limited to Columbia agar or Tryptic Soy agar. *Brucella* media typically comprise in a liter of medium 10 g pancreatic digest of casein, 10 g peptic digest of animal tissue, 1 g dextrose, 2 g yeast extract, 5 g sodium chloride and 0.1 g sodium bisulfite. Herein peptones supply organic nitrogen. The yeast extract is a potent source of the B vitamins. Dextrose is utilized as an energy source. Mueller-Hinton medium typically comprises in a liter of medium 2 g meat infusion, 17.5 g casein hydrolysate and 1.5 g starch. Such media are commercially available from companies such as Difco and Oxoid.

The present invention provides methods for the isolation and/or cultivation of *Helicobacter* species, which allow for the isolation and cultivation of a true *Helicobacter* isolate, more particularly a "Candidatus *Helicobacter suis*" isolate. It is understood, however, that other factors exist which influence the enrichment of *Helicobacter* species. Such factors include the way the sample comprising the *Helicobacter* species is obtained, more particularly, the way in which the stomach and the stomach wall is treated upon retrieval of the gastric material to minimize the contamination with other organisms.

Accordingly, particular embodiments of the isolation methods of the present invention further comprise a first step of providing a sample of gastric material comprising *Helicobacter* species under specific conditions. In one embodiment, a part of the stomach wall is incubated in acidic conditions which kill a considerable number of acid-labile organisms. In a further particular embodiment, the stomach wall is processed by isolating only the surface mucus of the stomach.

The media used in the cultivation and/or isolation methods of the present invention optionally comprise one or more additional components.

In particular embodiments of the methods of the present invention the cultivation medium further comprises active charcoal. Where a two-component system is used, the active charcoal is typically present at least in the solid component.

In particular embodiments of the methods of the present invention, the cultivation medium further comprises a biocompatible pH indicator which color changes at a pH between 5.5 and 6.0. For instance, phenol red, which turns yellow below pH 6.6 and red above pH 8, could be used. Such indicators are especially useful in plates comprising serum. Typically, in a two-component system, such a pH indicator is present in the solid component.

In particular embodiments, the methods of the isolation and/or cultivation methods of the present invention comprise the application of a sample comprising *Helicobacter* species on a two-component system, wherein the solid component comprises nutrients, growth factors and antibiotics, and is adjusted to a pH value between 4.7 and 7.0 (or more particularly between 5.0 and 6.0), while the liquid component only comprises nutrients without adjustment of the pH. Optionally, the pH of the liquid component is adjusted to a pH value between 4.7 and 7.0 (or, more particularly, between 5.0 and 6.0) and/or the liquid component also comprises growth factors and antibiotics.

Particular practical configurations can be considered for carrying out the methods of the present invention. Typically, isolation and cultivation is carried out in cultivation flasks or Petri dishes (plates). In particular embodiments the methods involve a two-component system, whereby the solid component covers the entire bottom of the cultivation recipient (with a typical thickness of between 1 mm and 5 mm) and the liquid or semi-liquid component is spread out over all or a part of the surface of the solid component.

In a very particular embodiment, the isolation is achieved in a Petri dish-like recipient with a diameter of 10 cm comprising between about 5 to 15 ml of a solid agar with the composition as described above. On top of the agar, between about 500 to 1000 µl of liquid broth is added as liquid component.

In another particular embodiment, the two-component system comprises a bottom agar without added nutrients, serum, or other additives, but which comprises a buffer at pH 5. On top of this bottom agar, a top agar is applied which contains all necessary ingredients for the cultivation of "Candidatus *Helicobacter suis*". Using this buffer, a minimum of expensive ingredients is used, while the pH of the top agar is kept stable by the presence of the underlying bottom agar.

The methods of the present invention can be used for the isolation and/or cultivation of *Helicobacter* species, more particularly "Candidatus *Helicobacter* suis". Typically, in the methods of the present invention, the sample of gastric material is incubated in the cultivation system for a period between 1 to 15 days, depending on the degree of contaminating microorganisms (e.g., fungi and/or bacteria) and the nutrient utilization of the medium. Where a solid medium is used, a sign of exhaustion of the medium is typically the appearance of translucent areas in the solid medium. Additionally or alternatively, the motility of *Helicobacter* species in the liquid medium can be assessed, whereby a reduced motility is indicative of exhaustion of the medium. Additionally or alternatively, the bacterial isolate can be transferred to a fresh plate when the pH of the cultivation medium (or the solid and/or liquid component) increases to a pH value of 6.0 or more.

Typically, the methods of the present invention involve the incubation of samples comprising *Helicobacter* species or isolates of *Helicobacter* species at 37° C. It was found that below 25 or above 40° C. degrees no growth of *Helicobacter* bacteria occurs. Generally, plates with *Helicobacter* species are grown under micro-aerobic conditions, i.e., between 2 and 8% oxygen, more particularly about 4-5% $O_2$. However, *Helicobacter* species do not grow under complete anaerobic conditions.

A particular embodiment of the methods for the isolation of *Helicobacter* species from a sample comprises the steps of:
a) applying the sample in a cultivation system comprising a solid and a liquid component,
  wherein at least the solid component is buffered at a pH between 5.0 and 6.0, and
  wherein the solid component comprises at least 10% serum or at least 7.5% blood, and
  wherein the solid and the liquid component comprise nutrients for the growth of fastidious bacteria, and
  wherein the solid and/or liquid component comprise at least one selective substance that inhibits the growth of fungi and/or Gram positive and/or Gram negative bacteria different from the *Helicobacter* species to be cultured,
the method further comprising the step of
b) incubating the sample in this system under micro-aerobic conditions.

Using the above described methods for the isolation and cultivation of *Helicobacter* species, true isolates of *Helicobacter* species, in particular "Candidatus *Helicobacter suis*", can be obtained from samples of gastric material. A Candidatus *Helicobacter suis* isolate obtained by methods according to the invention has been deposited in conformity with the requirements of the Budapest Treaty at the BCCM™/LMG Bacteria Collection, K. L. Ledeganckstraat 35, B-9000, Gent by Universiteit Gent on Jul. 30, 2008. It has been attributed number LMG P-24758. In addition, the methods of the present invention allow cultivation in vitro in bulk. In particular, cultivars can be obtained which can be passaged, more particularly passaged at least 1 time, more particularly at least twice, or at least 5 to 10 times and/or which can be maintained in culture (i.e., in vitro) at least 24 hours, more particularly at least 2 days, most particularly at least 10 to 25 days. It has been demonstrated that using the methods of the present invention, about 1 ml stomach mucus applied on one 10 cm bacterial plate generates a culture of between $10^6$ to $10^9$ bacteria/ml within 3 days. Upon passaging cultures can be diluted with a factor of 1 to 5. Accordingly, even with small-scale systems, high yields can be reached. However, in large-scale production, the yields can be further increased.

The methods of the present invention for the first time allow the generation of large amounts of true *Helicobacter* species isolates, in particular of "Candidatus *Helicobacter suis*". This is important as it allows the manufacture of vaccines using isolated "Candidatus *Helicobacter suis*" or antigen preparations obtained therefrom.

Accordingly, another aspect of the invention relates to the use of "Candidatus *Helicobacter suis*", such as those obtainable by the methods described herein for the production of antigenic preparations, which are useful as vaccines. Indeed, the present invention allows, for the first time, the generation of a vaccine based on true "Candidatus *Helicobacter suis*" isolates. Particular embodiments of the invention relate to the use of deposited culture LMG P-24758 for the production of antigenic preparation of Candidatus *Helicobacter suis*.

Antigen preparations of "Candidatus *Helicobacter suis*" isolates envisaged in the context of the present invention include both whole-cell bacterial preparations as preparations of components of "Candidatus *Helicobacter suis*" isolates, such as from the isolate LMG P-24758. Such antigen preparations may comprise whole-killed (inactive) bacteria, live-attenuated (weakened) bacteria or processed and/or artificial bacterial preparations or combinations thereof. Processed bacterial preparations include preparations of bacterial proteins, which are partially or completely purified and/or pre-treated. These can be used alone or in combination with artificial antigen preparations such as protein preparations which are either in part or entirely obtained by synthetic or recombinant methods.

According to a particular embodiment, the antigen preparations provided by the present invention comprise one or more antigens obtained from a "Candidatus *Helicobacter suis*" isolate. Most particularly, antigen preparations are envisaged comprising one or more antigens obtained from the isolate deposited as LMG P-24758. The advantage of working with antigen preparations obtained from isolates is purity, which reduces the chance of contamination with antigentic compounds of other organisms or bacterial species, thereby increasing the risk of unwanted side-effects of the antigenic preparation when injected into humans or other animals.

According to a particular embodiment, the antigen preparation is a cell lysate of "Candidatus *Helicobacter suis*", i.e., a mixture obtained upon lysis of bacterial cells. A particular example of a bacterial cell lysate is the soluble fraction of a sonicated bacterial culture, e.g., obtained after filtration. Alternatively or in addition, bacteria can be fragmented using a high-pressure homogenizer (e.g., Avestin model Emulsi-FlexC5).

Optionally, the cell lysate is further inactivated prior to or after sonication by one of a variety of known methods, such as but not limited to, treatment with formalin, binary ethyleneimine (BEI), beta propriolactone (BPL), gluteraldehyde, irradiation or heat. Generally, not all proteins in a lysate will provoke an immune response. Alternatively, the antigen preparation according to the present invention is obtained by fractionation and/or purification of one or more proteins from a lysate or bacterial culture medium to obtain a composition of enriched or purified antigens. Examples of isolated or purified bacterial proteins suitable in the context of the present invention are heat shock proteins and/or urease proteins, cagA and vacA.

Accordingly, another aspect of the present invention provides vaccines comprising the antigen preparations obtained from "Candidatus *Helicobacter suis*" isolates as described above. Most particularly, the invention provides vaccines comprising antigen preparations obtained from the Candidatus *Helicobacter suis* isolate deposited as LMG P-24758. The vaccines of the present invention comprising an antigen preparation of a "Candidatus *Helicobacter suis*" isolate can be used to obtain prophylactic or therapeutic immunity to infection by a *Helicobacter* species, more particularly "Candidatus *Helicobacter suis*".

The vaccine of the present invention optionally contains only the antigen preparation of the invention. Alternatively, the vaccine can comprise, in addition to the antigen preparation of the present invention, a suitable adjuvant. For example, the antigen preparations in the vaccines of the present invention can be formulated in or with liposomes, preferably neutral or anionic liposomes, microspheres, ISCOMs, or virus-like particles (VLPs), in order to promote the screening of the protein or of the polypeptide or to increase the immune response. Persons skilled in the art have these compounds available without difficulty; for example, see Liposomes: A Practical Approach. RRC New Ed, IRL press (1990).

Adjuvants other than liposomes may also be used. A large number are known to persons skilled in the art. The type of adjuvant will vary, depending on the type of antigen preparation and route of administration used. According to a particular embodiment of the present invention, the antigen preparation is a sonicated antigen solution which is administered intranasally with Cholera toxin (CT) or subcutaneously with saponin as adjuvant. Any adjuvant known in the art may be used in the vaccine composition, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), BIOSTIM® adjuvant (e.g., 01K2), the "Iscoms" of EP 109 942, EP 180 564 and EP 231 039, aluminum hydroxide, saponin, DEAE-dextran, neutral oils (such as miglyol), vegetable oils (such as arachid oil), liposomes, or Pluronic® polyols. Adjuvants include, but are not limited to, the RIBI adjuvant system (Ribi Inc.), alum, aluminum hydroxide gel, cholesterol, oil-in-water emulsions, water-in-oil emulsions such as, e.g., Freund's Complete and Incomplete Adjuvants, Block co-polymer (CytRx, Atlanta, Ga.), S-M (Chiron, Emeryville, Calif.), AMPHIGEN® adjuvant, saponin, Quil A, QS-21 (Cambridge Biotech Inc., Cambridge, Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others. According to a particular embodiment, a recombinant mutant of *Escherichia coli* heat-labile toxin is added to the antigen preparation prior to injection into the animal.

For parenteral administration, specific components may be added such as aluminum hydroxide, aluminum phosphate and aluminum hydroxyphosphate. One or more antigens of the antigen preparation may be absorbed or precipitated on an aluminum compound according to standard methods. Other adjuvants useful for parenteral administration include in particular polyphosphazene (WO 95/2415), DC-chol (3-beta-[N—(N',N'-dimethylaminomethane) carbamoyl) cholesterol] (U.S. Pat. No. 5,283,185 and WO 96/14831), QS-21 (WO 88/9336) and RIBI.

The components of the vaccines of the present invention may be manufactured conventionally. In particular, a polypeptide, a mixture or a molecule of DNA contained in the composition according to the invention is combined with a pharmaceutically acceptable diluent or carrier, e.g., water or a saline solution such as phosphate-buffered saline (PBS). In general, the diluent or the carrier is selected on the basis of the mode and route of administration and of standard pharmaceutical practices. Pharmaceutically acceptable diluents and carriers as well as all that is necessary for their use in pharmaceutical formulations are described in Remington's Pharmaceutical Sciences.

The vaccines of the present invention can be in solid or liquid form such as tablets, capsules, powders, solutions, suspensions, or emulsions.

The solid unit dosage forms can be of the conventional type. The solid form can be a capsule, such as an ordinary gelatin type containing the proteins or peptides of the present invention and a carrier, for example, lubricants and inert fillers such as lactose, sucrose, or cornstarch. In another embodiment, these compounds are tableted with conventional tablet bases such as lactose, sucrose, or corn starch in combination with binders like acacia, corn starch, or gelatin, disintegrating agents such as corn starch, potato starch, or alginic acid, and a lubricant like stearic acid or magnesium stearate.

The vaccines of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as propylene glycol or polyethylene glycol are preferred liquid carriers, particularly for injectable solutions.

For use as aerosols, the vaccines of the present invention comprising the antigen preparation in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The vaccine comprising an antigen preparation of "Candidatus *Helicobacter suis*" can be used for autologous or heterologous vaccination. In autologous vaccination using the vaccines of the present invention, the object is the protection against infection by "Candidatus *Helicobacter suis*". In heterologous vaccination, the object is to obtain by injection with an antigenic preparation of "Candidatus *Helicobacter suis*" protection against infection by one or more other *Helicobacter* species.

Accordingly, a further aspect of the present invention provides methods for the vaccination of humans and other animals using the vaccines of the present invention. The object of the vaccination schemes with the vaccines obtained from "Candidatus *Helicobacter suis*" isolates according to the present invention includes obtaining complete protection (sterilizing immunity) against *Helicobacter* spp., more particularly against "Candidatus *Helicobacter suis*" in an animal but also reducing the bacterial burden of *Helicobacter* spp., more particularly of "Candidatus *Helicobacter suis*" by at least 25, 40, 60, or 80% compared to prior to vaccination and/or compared to animals which have not received the vaccine of the present invention and are/have been subjected to the same infectious agent. Most particularly, the present invention relates to vaccines and vaccination strategies which ensure a protective effect or reduced bacterial burden for a prolonged period of time, such as during at least 4, 6, 10, 12 or more than 12 weeks.

The administration of the vaccines of the present invention may take place in a single dose or in a dose repeated once or several times after a certain period. The appropriate dosage varies according to various parameters, for example the individual treated (adult or child), the vaccinal antigen itself, the mode and frequency of administration, the presence or absence of adjuvant and, if present, the type of adjuvant and the desired effect (e.g., protection or treatment), as will be determined by persons skilled in the art. For example, where antigen preparations comprising inactivated whole "Candidatus *Helicobacter suis*" are used, suitable dosages include, but are not limited to dosages of 10 μg, 50 μg, 100 μg, 250 μg, 500 μg and 1 mg antigen preparation. Alternatively, dosages can be expressed in CFUs; 100 μg corresponds to about $10^7$ CFU. Crude antigen preparations (i.e., containing traces of culture medium) may require higher dosages to be effective than partly purified or purified preparations.

The methods of vaccination may include administration to the animal or human of one or more compositions prior to or after (oral) administration of the vaccine comprising the "Candidatus *Helicobacter suis*" antigen preparation according to the invention. Such components include compounds which reduce acid production in the stomach (e.g., Cimetidine (Tagamet®, GlaxoSmithKline; Genval, Belgium)).

The identification and quantification of infection and/or bacterial burden in an animal can be done in a number of ways. Classically, this is done by determining the presence of the infectious agent or a protein or DNA sequence thereof in a sample of body fluid or in urine or feces. Alternatively, the reaction of the immune system, e.g., the presence of antibodies to the infectious agent, can be measured. According to a particular embodiment of the invention, accurate diagnosis and quantification of *Helicobacter* infection is obtained by identification of "Candidatus *Helicobacter suis*" DNA, e.g., by PCR as described in the art (Fox and Lee (1997) *Lab. Anim. Sci.* 47, 222-255). Alternatively, a quantitative urease test is uses to quantify Candidatus *H. suis*. Briefly, mucosal tissue samples (approximately 0.5 cm$^2$) are immersed in 1,000 μl of CUTest (Temmler Pharma; Marburg, Germany) and incubated at 37° C. for approximately 3 hours (as described by Corthésy-Theulaz et al., (1995), *Gastroenterology* 109, 115-121). After centrifugation, the supernatant is used for spectrophotometric quantification at an optical density (OD) of 550 nm. The cut-off for discrimination between infection or not is calculated for each stomach region and corresponded to the mean plus two times the standard deviation (SD) of the absorbance values obtained with gastric biopsy specimens from non-challenged control animals. Values above this cut-off are considered evidence of colonization by "Candidatus *Helicobacter suis*".

As detailed above, the use of the vaccines of the present invention is envisaged both in autologous and heterologous vaccination schemes. According to one embodiment, methods are provided for the treatment and/or protection of humans and/or other animals against infection by one or more different *Helicobacter* species, optionally including "Candidatus *Helicobacter suis*". Particular embodiments of the present invention relate to the use of the vaccines obtained from "Candidatus *Helicobacter suis*" isolates to obtain prophylactic or therapeutic immunity to other *Helicobacter* spp. such as, but not limited to, *H. pyloris*, *H. bizzozeronii*, *H. felis* and *H. salomonii*. Other suitable *Helicobacter* species are *H. bilis*, *H. fenelliae*, *H. pametensis*, *H. nemestrinae*, *H. pametensis*, *H. acinonychis*, *H. pullorum*, *H. mustelae*, *H. hepaticus*, *H. cinaedi* and *H. canis*. Most particular embodiments of the present invention relate to the use of vaccines obtained from the Candidatus *Helicobacter suis* isolate LMG P-24572 to obtain prophylactic or therapeutic immunity to *Helicobacter* spp, including but not limited to Candidatus *Helicobacter suis*.

According to a particular embodiment, the invention provides methods of prophylactic and/or therapeutic protection against infection with "Candidatus *Helicobacter suis*", which comprise administering the vaccines of the present invention obtained from "Candidatus *Helicobacter suis*" isolates. More specifically, antigen preparations are provided for use in prophylactic vaccination, which ensure protection against *Helicobacter* spp., more particularly against "Candidatus *Helicobacter suis*", which protection is more than transient. In particular embodiments, methods of prophylactic and/or therapeutic protection against infection with "Candidatus *Helicobacter suis*" according to the invention comprise administering a vaccine obtained from the Candidatus *Helicobacter suis* isolate LMG P-24572.

Particular embodiments of the present invention also provide methods for therapeutic immunization when the organisms have already orientated the host immune response to their benefit.

The methods of immunization of the present invention include methods whereby the vaccine is administered through any suitable route, such as by mucosal (intranasal), parenteral, or intramuscular administration, oral, intradermal, intraperitoneal, intravenous, transdermal/transcutaneous, or subcutaneous administration. Suitable vaccination routes also comprise combination administrations (e.g., oral/intramuscular administration). According to specific embodiments of the invention, therapeutic immunization is performed by parenteral administration of the antigen preparations or vaccines of the invention. Parenteral immunization can mobilize cells from systemic origin that have not been already primed in one given direction by a *Helicobacter* infection (Guy et al. (1999) *Vaccine* 17, 1130-1135). According to another specific embodiment of the invention, intramuscular administration is used for efficient vaccination.

The different aspects of the present invention are illustrated by, but not limited to, the examples detailed hereafter.

EXAMPLES

Example 1

In vitro Isolation and Cultivation of "Candidatus *Helicobacter suis*"

In this example, "Candidatus *Helicobacter suis*" is isolated using a two-component cultivation system, whereby the solid component is a *Brucella* agar plate.

*Brucella* agar plates (Becton-Dickinson, Erembodegem, Belgium) were supplemented with Vitox supplement (Oxoid, Basingstoke, UK), Skirrow supplement (Oxoid), 20% fetal calf serum (FCS; QB Perbio Tattenhall, UK), 0.1% activated charcoal GR (AC; Merck, Darmstadt, Germany), 0.00001% crystal violet (Clin-Tech Ltd, Essex, UK) and 0.001% Nisin (Sigma-Aldrich, St-Louis, Mo., USA). after autoclaving but before gelling of the agar, 0, 0.2, 0.5 and 0.7 ml of a HCl solution (min. 37%; Riedel-de Haën, Seelze, Germany) was added to 500 ml of *Brucella* agar, resulting in pH values of 7.0, 6.3, 5.5 and 5.0, respectively. Unless otherwise indicated, *Brucella* plates with serum comprise 20% serum.

In this example the liquid component of the two-component cultivation system is *Brucella* broth, without addition of other supplements, serum and without adjustment of pH.

Day 0

Five swine stomachs (A to E) were collected from the slaughterhouse (Porc Meat N.V., Zele, Belgium) and stored at +4° C. until further use. They were opened at the curvature major and rinsed with tap water. One half of the stomach was subjected to acid treatment (submersion in a 1% HCl bath for 1 hour). Thereafter, only the surface mucus was collected by scraping the stomach with a glass slide. This mucus was collected into a sterile tube. Microscopic examination of the stomach mucus of the pigs showed that all stomachs were positive for "Candidatus *Helicobacter suis*".

The mucus was slightly liquefied with the *Brucella* broth comprising 20% serum (up to a volume of about 5 ml) and inoculated on four supplemented *Brucella* agar plates with serum with pH values of 5.0, 5.5, 6.3 and 7. The sample was inoculated onto the middle of the plate, and subsequently three drops of *Brucella* broth (about 150 μl) were added onto the middle of the mucus sample. Four plates per pig in total were incubated overnight in a micro-aerobic atmosphere at 37° C. The micro-aerobic environment was created by evacuating 80% of the normal atmosphere and introducing a gas mixture of 8% $CO_2$, 8% $H_2$ and 84% $N_2$.

Day 1

Primary isolation of motile spiral bacteria (indicating the presence of *Helicobacter* species) was successful for four of the five stomach samples. For stomach D, there was insufficient growth on day 1. Plates, which were dried out, were slightly humidified using *Brucella* broth with serum.

Day 2

It was observed that for all stomachs, the plates in which the agar was at pH 7 and 6.3 were contaminated with other bacteria. Broth from these plates was filtered (using a 0.65 μm pore filter) and passaged onto new agar plates of the same pH.

Only some of the plates with pH 5.5 or 5.0 were contaminated, in which case the broth was also filtered and passaged to new plates. When no contamination was seen, the plates were further incubated. This was the case for the plates at pH 5.0 of stomach samples D and E.

When the pore size of the 0.65-μm pore filters was too small to filter the medium without clogging, the filtration was performed with 0.8-μm filters. This was the case for contaminated plates of pH 7, 6.3 and 5.5 of stomach sample E.

Day 3

Those plates, which were inoculated with filtered medium on day 2, were mostly negative for contaminating bacterial growth.

The original non-contaminated, non-filtered pH 5.0 plate from stomach E was analyzed microscopically and showed many "Candidatus *Helicobacter suis*" bacteria with a remarkable motility, the number of which was estimated to be about $10^8$ or $10^9$/ml. The broth culture (about 500 μl) was transferred onto a new agar medium of pH 5.

Day 4

The original pH 5.0 plate of stomach E and its passaged plate were overgrown with contaminants. Broth from these plates was transferred onto new agar plates using 0.65-μm pore filters.

Many plates from the other stomachs were also contaminated and discarded. From stomach A, two filter-passaged plates were negative for bacterial contamination and were further incubated. From stomachs B, C and E, one filter-passaged plate was negative and further incubated.

From stomach D, the pH 5.0 plate was still negative for contaminating bacterial growth and was further incubated.

Day 5

All filter-passaged plates, which were negative on day 4 for "Candidatus *Helicobacter suis*", were still negative for *Helicobacter* and were further incubated. Some plates showed contaminating bacteria.

Day 7

The broth on top of the pH 5.0 plate from stomach D showed viable and motile "Candidatus *Helicobacter suis*" bacteria, the number of which was estimated to be $10^6$/ml. The mucus was not visibly contaminated with other bacteria. This plate was further incubated.

Day 8

From stomach D, the original plate of pH 5.0 showed further growth of "Candidatus *Helicobacter suis*" bacteria. The broth was transferred onto an agar plate of pH 7. On the original plate, 500 μl of *Brucella* broth with serum was added.

Day 11

The passage of sample D of day 8 onto a pH 7 plate was negative for *Helicobacter* growth. The original plate of pH 5.0 still showed a viable culture of "Candidatus *Helicobacter suis*" (estimated 108 bacteria/ml). This broth was transferred onto a pH 5.0 plate, and an equal amount of *Brucella* broth with serum was added.

On the original plate, 500 μl of *Brucella* broth with serum was added.

Day 13

The passage on the pH 5.0 plate on day 11 was successful for the isolate originating from sample D. The broth contained motile *Helicobacter* (estimated $10^8$ bacteria/ml). Broth was again transferred onto a pH 5.0 plate, while the plate of the first passage was humidified with 1 ml of *Brucella* broth with serum. The broth on the original plate of sample D also contained a viable culture, of which about 200 μl was frozen in an equal amount of LYM (¼ BHI broth+¾ horse serum+7.5% (w/v) glucose) at −70° C. Again, 500 μl of *Brucella* broth with serum was added before further incubation.

From stomachs B and C, filter passages on day 4 onto plates of pH 5 were slightly positive for "Candidatus *Helicobacter suis*".

Day 14

The frozen culture D of day 13 was thawed and applied on a supplemented *Brucella* agar plate with pH 5 and incubated in a micro-aerobic atmosphere.

Day 15

The second passage of sample D (HS1) was positive for "Candidatus *Helicobacter suis*" (estimated $10^8$ bacteria/ml). Broth of this plate (about 500 μl) as well as broth from the original sample D pH 5.0 plate was added to an equal volume of *Brucella* broth, 3 vol. FCS and 7.5% (w/v) glucose, and frozen at −70° C.

The first passage contained more broth (about 1 ml) and was passaged onto two fresh agar plates of pH 5. Equal amounts of *Brucella* broth with serum were added.

The filter passage of B was still slightly positive for *Helicobacter*, whilst the filter passage of C contained about $10^6$ bacteria/ml. These plates were slightly humidified with *Brucella* broth with serum.

Day 17

The original pH 5.0 plate of sample D was again positive for *Helicobacter*, but they were less motile. As the medium of the agar was probably exhausted, the broth was transferred again onto a fresh agar plate (pH 5) with medium and the original plate was discarded.

The second passage of D was positive and broth was again transferred onto a new agar plate, and the plate was again humidified with supplemented *Brucella* broth and further incubated.

Of the filter-passaged plates of B and C, broth was transferred onto new agar plates of pH 5. On the original plates *Brucella* broth with serum was added.

Day 19

Samples were taken from cultures derived from stomachs D (isolate HS1), C (isolate HS2) and B (isolate HS3). DNA was extracted from bacterial cells using DNeasy Tissue kit (Qiagen). PCR was performed using Candidatus *H. suis*-specific primers (De Groote et al., 1999 *Bacteriology* 49, 1769-1777; 2000 *J. Clin. Microbiol.* 38, 1131-1135). Agarose gel electrophoresis showed a 433 bp long PCR fragment for all three isolates. DNA from a culture of in vivo mouse passaged "Candidatus *Helicobacter suis*" was used as a positive control.

The plate inoculated on day 14 with thawed material from HS1, was positive for "Candidatus *Helicobacter suis*". The broth was transferred on two new plates (second passage).

The second passage of HS1 was mixed with an equal amount of 1 vol. *Brucella* broth, 3 vol. FCS, 7.5% (w/v) glucose and frozen at −70° C.

The broth from the third passage of HS1 was positive and transferred onto a new plate.

Day 20

For HS2 and HS3, the broth from the second passages was mixed with an equal amount of 1 vol. *Brucella* broth, 3 vol. FCS, and 7.5% (w/v) glucose and frozen at −70° C.

Day 22

On the plate inoculated with thawed material from HS1, "Candidatus *Helicobacter suis*" did not grow much further. The passages of day 19 of this isolate, however, showed more *Helicobacter*.

The fourth passage of day 19 from the original culture did not show many bacteria.

The second passages of day 17 of cultures deriving from C and D showed many "Candidatus *Helicobacter suis*" bacteria. The broth from sample C(HS2) was transferred onto two new plates, and equal volumes of supplemented *Brucella* broth were added. The broth from sample B (HS3) was transferred onto one new plate, and an equal volume of supplemented *Brucella* broth was added.

Day 25

For HS1, the second passage of day 15 showed very few Candidatus *H. suis*. All broth was transferred to a fresh agar plate (pH 5.0) and the old plate was discarded.

The third passage of day 17 and the fourth passage of day 19 were negative and discarded.

The plate inoculated on day 14 with thawed material from HS1 showed a grown culture of "Candidatus *Helicobacter suis*" and this broth was inoculated onto two new plates and with *Brucella* broth with serum. The second passages of day 19 of this isolate were also inoculated onto two plates each.

For HS2 and HS3, the second passages of day 17 showed less motile *Helicobacter*. The plates showed translucent areas and were probably exhausted. All broth was transferred onto a new plate and the old plate was discarded. The third passages showed good cultures which were transferred onto two new plates per isolate.

Day 27 and Following Days

From the third and fourth passages of HS1, broth was frozen in an equal volume of 1 vol. *Brucella* broth, 3 vol. of FCS and 7.5% (w/v) glucose. The broth of the second passage of day 22 was inoculated onto a new agar plate.

For HS2 and HS3, third and fourth passages were inoculated onto a new agar plate. Cultures were passaged continuously every two or three days and broth cultures were frozen regularly as described above.

The 16S rRNA gene of isolates HS1, HS2 and HS3 was amplified using primers complementary to the conserved edges. Consensus primers αβ-NOT (5'-tcaaactaggaccgagtc-3') [SEQ ID NO:1] and ωMB (5'-taccttgttacttcacccca-3') [SEQ ID NO:2] were used, as previously described (Baele et al., (2001) *J. Appl. Microbiol.* 91, 488-491). A 1500 bp amplicon amplified in this PCR reaction was sequenced using primers pD (5'-cagcagccgcggtaatac-3') [SEQ ID NO: 3], γ* (5'-ctcctacggaggcagcagt-3') [SEQ ID NO:4], 3 (5'-gttgcgctcgttgcgggact-3') [SEQ ID NO: 5] and O* (5'-aactcaaaggaattgacgg-3') [SEQ ID NO: 6], as described in Coenye et al. (1999) *Int. J. Syst. Evol. Microbiol.* 49, 405-413). Sequence analysis was performed using the ABI Prism™ 3100 Genetic Analyzer (Applied Biosystems, Lennik, Belgium) and sequences were aligned with GenBank using BLAST. The sequence revealed 99% similarity with the sequence of "Candidatus *Helicobacter suis*" in GenBank (AF127028).

In the experimental settings as described above, primary isolation was most successful on plates containing medium of lower pH values (5.0 or 5.5). Under these conditions the growth of contaminating bacteria was diminished.

Isolation of "Candidatus *Helicobacter suis*" from stomach E was successful. On the third day after inoculation, a pure culture of about $10^8$ or $10^9$/ml was seen under the microscope. Contaminants growing on the mucus were mixed with the broth containing *Helicobacter*, which was unavoidable, when transferring the broth onto a new agar plate.

From stomachs B, C and D, pure cultures of "Candidatus *Helicobacter suis*" were obtained. A species-specific PCR amplifying a 16S rDNA fragment confirmed the species identity. Sequencing of the whole 16S rDNA gene revealed 99% similarity with the sequence of "Candidatus *Helicobacter suis*" in GenBank.

For isolate HS1, originating from D, primary isolation of a pure broth culture of "Candidatus *Helicobacter suis*" was obtained after 7 days of incubation. Transferring the broth onto a plate with the same medium at pH 7 did not result in growth. Passaging to a plate of pH 5.0 was successful. Broth showing viable and motile *Helicobacter* was divided into two equal volumes and transferred onto two fresh agar plates. Supplementation with an equal amount of *Brucella* broth (with 20% FCS) resulted in good growth of the bacteria.

"Candidatus *Helicobacter suis*" cells in broth can be frozen at −70° C. in an equal amount of 1 vol. *Brucella* broth, 3 vol. FCS and 7.5% (w/v) glucose. After thawing one vial that was frozen, Candidatus *H. suis* was successfully regrown on the same medium.

For isolates HS2 and HS3, originating from stomach B and C, respectively, primary cultures on media with pH 5.0 were slightly contaminated with other bacteria. The broth was then brought onto a 0.65-μm pore filter and inoculated on new agar plates of pH 5. After 11 days of incubation, these plates were positive for *Helicobacter* growth. After again 4 days of incubation, the broth contained enough *Helicobacter* to passage the strains. Second and third passage cultures were obtained after 5 and 3 days of incubation, respectively.

Example 2

Effect of Temperature and Environment on "Candidatus *Helicobacter suis*" Growth In this and all following experiments, the optimization of culture medium and growth conditions was evaluated on "Candidatus *Helicobacter suis*" isolates HS1, HS2 and HS3. Details on the isolation of these strains are given in example 1.

Isolates HS1 and HS3 were inoculated each onto six *Brucella* agar plates as described in the previous example, (i.e., comprising 20% FCS and adjusted to pH 5.0). Plates were overlaid with *Brucella* broth supplemented with Vitox supplement, fungizone, 20% FCS and 0.7 ml HCl per 500 mL of broth (resulting in a pH of 5).

Three plates were incubated in a micro-aerobic environment created in jars using the Campygen™ 2.5 L (Oxoid) system, at 37° C., 25° C. and 42° C. respectively.

The other three plates were incubated at 37° C. in an aerobic, anaerobic and 5% $CO_2$-supplemented atmosphere, respectively. After six days of incubation, growth was evaluated by microscopic examination of the overlaying broth.

In a 5% $CO_2$-supplemented environment and an aerobic atmosphere, no growth was obtained. In an anaerobic environment, only very few bacteria were seen.

In micro-aerobic conditions, good growth was seen at 37° C., while at 25° C. or 42° C., no growth was obtained.

Example 3

Effect of Activated Charcoal and Growth Factors on "Candidatus *Helicobacter suis*" Growth Isolates HS1 and HS3 were inoculated on Mueller-Hinton agar plates, supplemented with Vitox supplement, Skirrow supplement, fungizone and 20% fetal calf serum, adjusted to pH 5.0.

To these plates, the following components were added. One type of plates (MH1), in addition contained Vitox supplement but no activated charcoal. Another type of plates (MH2) in addition contained activated charcoal but no Vitox supplement, while a third type of plates (MH3) contained both Vitox supplement and activated charcoal.

After three and seven days of incubation at 37° C. in micro-aerobic conditions in a closed circuit, created by evacuating 80% of the normal atmosphere and introducing a gas mixture of 8% $CO_2$, 8% $H_2$ and 84% $N_2$, growth was evaluated by microscopic examination of the overlaying broth.

Media MH1 and MH3 showed good growth of isolates HS1 and HS3. On MH2, no growth was seen for either of the isolates.

When using Mueller Hinton media, the omission of Vitox growth supplement impedes growth while the presence or absence of activated charcoal has no or little effect.

Example 4

Effect of Alternative Nutrient Compositions on "Candidatus *Helicobacter suis*" Growth In the present experiment, Mueller-Hinton agar or *Brucella* agar was replaced by another medium for fastidious bacteria, namely bovine Brain Heart Infusion (BHI) agar plates. These plates were supplemented with Vitox supplement, Skirrow supplement, fungizone and 20% fetal calf serum and were adjusted to pH 5 with concentrated HCl.

Plates were overlaid with BHI broth, supplemented with 20% fetal calf serum. After four days of incubation on these plates of isolates HS1 and HS2, at 37° C. in a micro-aerobic environment, growth was confirmed by microscopic examination of the overlaying broth.

Example 5

Effect of Serum in Plates on "Candidatus *Helicobacter suis*" Growth

Isolate HS1 was inoculated on a) Mueller-Hinton agar plates supplemented with Skirrow supplement, fungizone adjusted to pH 5.0 with concentrated HCl and on b) the same plates as in a) comprising in addition 20% FCS and Vitox supplement.

Plates were overlaid with Mueller-Hinton broth, supplemented with Vitox supplement, Skirrow supplement, fungizone, 20% FCS and adjusted to pH 5.0 with concentrated HCl.

After three days of incubation at 37° C. in a micro-aerobic environment on plates a) or b), growth was evaluated by microscopic examination of the broth. Coccoid forms only were observed on plates without serum in the agar (a). Good growth of HS1 was obtained on plates comprising the standard amount of 20% FCS (b).

Isolate HS1 was then inoculated on c) Mueller-Hinton agar plates supplemented with Skirrow supplement, fungizone adjusted to pH 5.0 with concentrated HCl, and overlaid with Mueller-Hinton broth, supplemented with Vitox supplement, Skirrow supplement, fungizone, 40% FCS and adjusted to pH 5.0 with concentrated HCl.

After four days of incubation at 37° C. in a micro-aerobic environment on plates c), growth was evaluated by microscopic examination of the broth. Again, coccoid forms only were observed.

Example 6

Effect of Blood on "Candidatus *Helicobacter suis*" Growth

The use of blood instead of serum was evaluated by replacing 20% FCS in the plates with 10% sheep or 10% horse blood. The pH of the plates was adjusted to pH 5.0 with concentrated HCl.

The plates were overlaid with Mueller-Hinton broth

After four days of incubation at 37° C. in a micro-aerobic environment, growth was evaluated by microscopic examination of the overlaying broth.

Very good growth of both isolates was obtained, regardless of the origin of the blood used, indicating that blood can be added to the culture medium, instead of serum.

Example 7

Effect of the Concentration of Blood on "Candidatus *Helicobacter suis*"

Isolate HS1 was inoculated on Mueller-Hinton agar plates supplemented with Vitox supplement, Skirrow supplement, fungizone and differing amounts of horse blood (2.5%, 5%, 7%, 10% and 15% (v/v)). The pH of the plates was adjusted to pH 5.0 with concentrated HCl.

Plates were overlaid with Mueller-Hinton broth without further supplements.

After three days of incubation at 37° C. in a micro-aerobic environment, growth was evaluated by microscopic examination of the broth. On plates with 2.5%, 5% or 7% horse blood, only coccoid forms were seen. Growth of "Candidatus Helicobacter suis" was observed on the plates with 10% or 15% horse blood. Of the plates with 10 and 15% blood, broth was then subcultured onto new agar plates with blood concentrations between 2.5 and 15% containing the same medium, by inoculating 1 ml of culture and adding 1 ml of fresh broth. Plates were further incubated at the same conditions for another three days. Again, viable cultures were only observed on plates with 10% or 15% horse blood.

First subcultures were again transferred onto new agar plates as described above. Growth was evaluated after 4 and 7 days of incubation, respectively. Second subcultures on media with pH 5.3 and 4.8 were transferred onto fresh agar plates. First subcultures on media with pH of 4.75, 4.5, 4.4 and 4 were also transferred onto fresh plates. Growth was evaluated after 3 and 7 days of incubation, respectively.

TABLE 1

Growth of H. suis isolate HS1 after subculturing on Mueller-Hinton media with different pH values

| pH Agar | pH Broth | Primary culture | | first subculture | | | second subculture | | third subculture | |
|---|---|---|---|---|---|---|---|---|---|---|
| | | 3 days | 5 days | 2 days | 4 days | 8 days | 4 days | 7 days | 3 days | 7 days |
| 5.0 | 7.0 | ++++ | ND | ND | ND | ND | ND | ND | ND | ND |
| 6.8 | 6.8 | +++ | ++ | ++ | + | − | ND | ND | ND | ND |
| 6.7 | 6.7 | ++ | ++ | ++ | +++ | + | − | +/− | ND | ND |
| 6.6 | 6.6 | ++ | + | ++ | +++ | + | − | − | ND | ND |
| 6.5 | 6.5 | ++ | + | ++ | +++ | + | + | − | ND | ND |
| 6.2 | 6.3 | ++ | ++++ | ++++ | +++ | ++ | + | − | ND | ND |
| 5.9 | 6.1 | +++ | ++++ | ++++ | +++ | ++ | ++ | + | ND | ND |
| 5.4 | 5.3 | +++ | ++++ | ++++ | +++ | +++ | ++++ | + | +++ | ND |
| 4.8 | 4.8 | +++ | ++++ | + | +++ | ++++ | ++++ | +++ | +++ | ND |
| 4.7 | 4.6 | +++ | ++ | + | + | ++ | ND | ND | ++++ | ++++ |
| 4.7 | 4.4 | ++ | ++ | + | + | ++ | ND | ND | + | + |
| 4.4 | 4.4 | + | + | + | + | ++ | ND | ND | ++ | − |
| 4.1 | 4.2 | + | + | + | + | ++ | ND | ND | + | − |
| 3.7 | 3.9 | − | − | + | − | − | ND | ND | ND | ND |
| 3.5 | 3.6 | − | − | + | − | − | ND | ND | ND | ND |

ND: Not Done;
++++: very good growth;
+++: good growth;
++: moderate growth;
+: weak growth;
+/−: very few bacteria;
−: no growth.

Example 8

Effect of the pH on "Candidatus Helicobacter suis" Growth

Isolate HS1 was inoculated on Mueller-Hinton agar plates supplemented with Vitox supplement, Skirrow supplement, fungizone and 20% FCS and adjusted to different pH values.

Plates were overlaid with Mueller-Hinton broth, supplemented with Vitox supplement, Skirrow supplement, fungizone and 20% FCS adjusted with concentrated HCl to different pH values. The specific combinations of pH of agar and broth are shown in Table 1.

After three days of incubation at 37° C. in a micro-aerobic environment, growth was evaluated by microscopic examination of the broth. Broth was then subcultured onto new agar plates by inoculating 1 ml of the culture and adding 1 ml of fresh broth with the same pH value. Primary cultures and subcultures were evaluated after 2 days of incubation.

The isolate used (HS1) could not grow on media with a pH below 4 (pH 3.5 or 3.7). Primary cultures were obtained on media with pH values ranging from 4 to 7. Subculturing was successful on these plates, however, repeated subculturing was only successful on media with pH values ranging from 4.7 to 6. Growth of "Candidatus Helicobacter suis" is possible on media with a pH ranging from 4.5 to 6.0 with an optimum at pH values 4.7 and 5.5.

Summarizing, "Candidatus Helicobacter suis" has an optimal growth at 37° C. in micro-aerobic conditions on a two-component system. The solid component comprises a medium for fastidious micro-organisms (such as Brucella agar, Brain Heart Infusion agar or Mueller-Hinton agar), supplemented with fetal calf serum or blood, growth supplements and adjusted to pH 5.0. Plates are overlaid with the liquid component which is a broth of a growth medium for fastidious micro-organisms (such as Brucella broth, Brain Heart Infusion broth or Mueller-Hinton broth) with or without growth supplements, serum or pH adjustment.

Example 9

Immunogenicity of Sonicated Filtrate Antigens of in vitro Cultivated H. suis

Three-week old male SPF BALB/c mice (free from Helicobacter spp.) were housed in autoclaved filter top cages (5 animals/cage), fed with a commercial diet and provided water ad libitum for 2-3 weeks prior to initiation of the experiment.

At the time of the allotment, mice were housed in individual cages. A Candidatus *H. suis* cultivar was isolated and cultivated using the method described in Example 1 herein. Antigen was prepared by sonicating a bacterial suspension and filtering it through a 0.22-µm pore filter. Protein concentration was determined by the Lowry assay. The *H. suis* preparation had a concentration of 1.838 mg/ml.

For each dose of vaccine, 100 µg of protein was used. For intranasal (IN) administration of the antigens, 5 µg of cholera toxin (Sigma) was added per dose.

Swine stomachs were collected from the slaughterhouse and homogenized. These stomach homogenates were used to infect BALB/c mice for propagating *H. suis* in vivo. Passaging in mice was performed every two weeks with whole urease-positive mouse stomachs homogenized in LYM (5 mL LYM/stomach) (LYM used in this example consists of 2 volumes of horse serum, 1 volume of Brain Heart Infusion broth and 10% glucose). PCR confirmed the presence of *H. suis* in each passage. The fourth mouse passage was performed in 10 BALB/c mice. From these 10 mice the urease-positive stomachs were pooled and homogenized. The homogenate was frozen at −70° C.

The titer of the frozen stock was determined after thawing the frozen stock. Fifteen minutes after thawing at 37° C., serial dilutions of homogenate in LYM were made and intragastrically (IG) inoculated in mice to determine the 100% mouse infection dose level.

Groups of 5 mice were vaccinated and inoculated according to Table 2.

TABLE 2

Study design of vaccination experiment

| Group | IVP | Route | N | Vaccination | Challenge | *Fecal Sample Collection | Necropsy Blood Sample |
|---|---|---|---|---|---|---|---|
| T01 | Saline | IN | 5 | D21, D42 | D70 | D88-D91 | D119-120 |
| T02 | SF *H. suis* | IN | 5 | D21, D42 | D70 | NA | D119-120 |
| T03 | SF *H. suis* | SC | 5 | D0, D21, D42 | D70 | NA | D119-120 |
| T10 | NVNC | NA | 5 | D0, D21, D42 | D70 | D88-D91 | D119-120 |

IVP = Investigated veterinary product
SF = Sonicated filtrate preparation
SC = Subcutaneous injection;
IN = Intranasal administration
NVNC = Non-vaccinated, non-challenged mice;
NA = Not applicable Urease activity in the stomach of mice is indicative of colonization of *Helicobacter* bacteria and was assessed using the method of Corthésy-Theulaz et al. (1995), cited above. One half of the stomach was immersed in 500 µl of CUTest (Temmier Pharma) and incubated at 37° C. for 3 h. After centrifugation (5 min, 100×g), the supernatant was used for spectrophotometric quantification at an OD of 550 nm. The cut-off value was calculated in each experiment and corresponded to the mean+5 S.D. of the absorbance values obtained with gastric samples of non-immunized, non-challenged mice.

DNA from mucosal tissue samples was extracted with the Dneasy Tissue kit (Qiagen, Hilden, Germany). PCR for specific detection of *H. suis* was performed as described previously (De Groote et al., 2000, cited above)

The mean urease values per stomach tissue of vaccinated mice were compared with these of non-vaccinated mice. The percentage of stomachs PCR positive for *H. suis* was compared between non-vaccinated/challenged mice vs. vaccinated-challenged controls. The stomachs of non-challenged mice are PCR and urease negative.

Blood samples for serological analyses were taken at necropsy.

Fecal samples of mice of group T01 were all positive at D (Day) 88-D91. Fecal samples of mice of group T10 were all negative at D88-D91.

The results of urease and PCR tests are summarized in Table 3.

TABLE 3

Results of the urease test and PCR test of mice vaccinated with in vitro cultivated *H. suis* antigens and challenged with *H. suis*

| Group | IVP | Mean Urease values | PCR Antrum # | PCR Fundus # |
|---|---|---|---|---|
| T01 | Saline | 1.63 | 5/5 | 5/5 |
| T02 | *H. suis* IN SF | 0.136 | 1/5 | 3/5 |
| T03 | *H. suis* SC SF | 0.341 | 5/5 | 5/5 |
| T10 | NVNC | 0.118 | 0/5 | 0/5 |

Number of PCR positive samples/total samples

The above results show that intranasal and subcutaneous immunization caused a decrease in mean urease activity values in the stomachs of all vaccinated animals. The urease activity levels were lower in the intranasally vaccinated animals. PCR testing on stomach samples showed a partial clearance of *H. suis* DNA in the intranasally vaccinated group. Subcutaneous immunization of mice showed no reduction in PCR detection of *H. suis*. A protective effect of the vaccine prepared using in vitro grown *H. suis* is achieved.

Example 10

Reduction of Candidatus *Helicobacter suis* Colonization by Vaccination of Pigs Using Antigens Obtained from "Candidatus *Helicobacter suis*" Isolates The safety and efficacy of the "Candidatus *Helicobacter suis*" vaccine was determined. The "Candidatus *Helicobacter suis*" antigen was inactivated and disrupted by sonication, followed by sterile filtration and formulation with an oil-in-water emulsion adjuvant. The antigen dose was determined based on the amount of total protein present.

Study Design

Sows were selected from a herd free of "Candidatus *Helicobacter suis*" infection, as determined by PCR and urease screening of stomachs from herdmates at slaughter. Piglets from these sows were allotted to one of three groups: a saline control, "Candidatus *Helicobacter suis*" vaccine group, or a third group (NTX; untreated) (Table 4). The study was a completely randomized design, and each animal was the experimental unit. Following weaning, sows were euthanized and the stomach analyzed by a quantitative urease test and PCR for the presence of *H. suis*. Nine piglets from a sow found urease and PCR positive for *H. suis* in the stomach were excluded from the study.

TABLE 4

Study Design

| Treatment | Vaccine | N | Regimen | Age at Vaccination[#] | Challenge |
|---|---|---|---|---|---|
| T01 | Saline | 16 | IM | 1, 3, 5 wk | 5, 6, 7, 8 wk |
| T02 | H. suis | 16 | IM | 1, 3, 5 wk | 5, 6, 7, 8 wk |
| NTX[+] | NA | 4 | NA | NA | NA |

[#]Intramuscular (IM) injection in the neck, alternately left (wk1), right (wk 3), and then left (wk 5).
All pigs were euthanized at 14 weeks of age.
[+]NTX = not treated.

TABLE 5

Antigen and IVP Preparation

| IVP* | Antigen Dose | Adjuvant[^] per Dose | Volume per Dose |
|---|---|---|---|
| Saline (PBS) | NA | 1 mL | 2 mL |
| H. suis | 250 μg first two doses; 500 μg third dose | 1 mL | 2 mL |

*IVP = Investigational Veterinary Product (Vaccine)
[^]The adjuvant- a final concentration of 5% Oil-water emulsions- was be mixed 1:1 with the antigen.

Vaccination and Challenge

Pigs were vaccinated by intramuscular injection in the neck at 1, 3, and 5 weeks of age (Table 5). Control pigs were vaccinated at the same time with an equal volume of saline. Pigs were observed for clinical signs 1 day before and two days after vaccination, and within 1-hour post vaccination. For the *H. suis* challenge, homogenates of scrapings of the upper cell layers and mucus of the antrum of gastric samples which have been tested positive for *H. suis* (using urease test) were used. To confirm the viability and dose of the pig stomach homogenate used as challenge material, an aliquot of each challenge material was administered to five week-old male SPF BALB/c mice free from *H. suis* infection. Mice were sacrificed 2 weeks later and the stomach contents screened by urease and PCR for the presence of *H. suis*.

Post-Challenge Methods and Scoring

To determine infection, intestinal tracts were dissected and the mucosal surface from the pars oesophagea was macroscopically examined. Lesions were scored on a scale of 0-5 using the method of Hessing et al. (1992, *Tijdschrift voor Diergeneeskunde* 117, 445-450). Briefly, scores were recorded as follows: 0=Intact mucosa; 1=Mild hyperkeratosis (<50% surface area); 2=Severe hyperkeratosis (≧50% of surface area); 3=Hyperkeratosis and a few small erosions (less than 5 and shorter than 2.5 cm); 4=Hyperkeratosis and extensive erosions (more than 5 erosions and/or longer than 2.5 cm); 5=Hyperkeratosis and very large erosions (more than 10 erosions or longer than 5 cm) and/or ulcers. Each stomach was also scored using a visual analog scale from 0-100 mm where 0=No lesion and 100=Perforating ulcer.

After scoring, several sites from the glandular mucosa (approximately 0.5 cm$^2$) from each stomach were sampled by PCR, TM-PCR (TaqMan® quantitative PCR), quantitative urease test, and histology. PCR for specific detection "Candidatus *Helicobacter suis*" was performed as described by De Groote et al. (2000, above). The bacterial load was tested by the quantitative urease test described herein. Stomach tissue scrapings were tested using TM-PCR with both *Helicobacter* genus specific and *H. suis* specific probes. DNA from tissue biopsies was extracted according to manufacturer's directions using the Qiagen Blood and Tissue kit. Three (3) sets of primers and probes were used to evaluate each sample: *Helicobacter* genus primers/probe and *Helicobacter suis* primers/probe recognizing appropriate sequences in the 16S region and the Applied Biosystems Control Reagent kit recognizing the 18S region of eukaryotic cells. TM PCR master mix (Applied Biosystems) was used according to manufacturer's directions. DNA was added to the master mix in appropriate concentrations and assayed in the 7900HT Real Time PCR Instrument (Applied Biosystems) using the default PCR program (holds of 50° C. for 2 minutes followed by 95° C. for 10 minutes then 40 cycles of 95° C. for 15 seconds and 60° C. for 1 minute). The copy number per sample was determined by comparison to a plasmid standard curve containing the appropriate sequences.

Results: Urease

Urease optical density scores were determined for the three (3) major regions of the stomach: antrum, cardia, and fundus. Tables 6-8). The *H. suis* vaccine reduced urease scores compared to saline controls in both the cardia and fundus (P=0.0025 and 0.0199 respectively). The stomachs of NTX pigs were negative as determined by PCR and urease.

TABLE 6

Least squares mean gastric antrum urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 65 | 0.88[a] | 0.315 | 0.48 | 1.60 | 0.05 to 2.31 |
| T02 | 73 | 1.23[b] | 0.394 | 0.72 | 2.10 | 0.1 to 2.48 |

Scores with different letters are statistically significantly different from each other (P ≦ 0.10)

TABLE 7

Least squares mean gastric cardia urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 36 | 0.91[a] | 0.323 | 0.29 | 2.91 | 0.09 to 2.18 |
| T02 | 35 | 0.38[b] | 0.134 | 0.12 | 1.19 | 0.05 to 2.17 |

Scores with different letters are statistically significantly different from each other (P = 0.0025)

TABLE 8

Least squares mean gastric fundus urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 32 | 0.77$^{ab}$ | 0.191 | 0.39 | 1.52 | 0.08 to 2.19 |
| T02 | 36 | 0.46$^c$ | 0.110 | 0.23 | 0.93 | 0.07 to 1.89 |

Scores with different letters are statistically significantly different from each other (P = 0.0199)

Results: PCR

All gastric regional sites were positive for the presence of *H. suis* as determined by qualitative PCR assay. All NTX gastric biopsies were negative (Table 9).

TABLE 9

PCR positive/negative score for gastric regional biopsies

| | Group | | |
|---|---|---|---|
| | NTX | T01 | T02 |
| | | N | |
| % Positive | 4 | 13 | 14 |
| Antrum | 0 | 100 | 100 |
| Cardia | 0 | 100 | 100 |
| Fundus | 0 | 100 | 100 |

Quantitative PCR for Gastric Regional Biopsies

DNA derived from 0.25 cm$^2$ biopsy samples, a total of 2 per antrum per pig, or one (1) per cardia or fundus per pig, was used to detect the level of *Helicobacter* DNA. While there were no statistically significant differences for TM-PCR for gastric antrum, fundus, or cardia between vaccine groups (Tables 10-12), there was a numerical reduction in the level of *Helicobacter* DNA detected in the fundus and cardia (Tables 11 & 12).

TABLE 10

TM-PCR for gastric antrum

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 30 | 0.03 | 0.041 | 0.00 | 0.28 | 0 to 4.24 |
| T02 | 32 | 0.06 | 0.075 | 0.01 | 0.51 | 0 to 13.64 |

TABLE 11

TM-PCR for gastric cardia

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 16 | 0.02 | 0.014 | 0.00 | 0.08 | 0 to 2.48 |
| T02 | 16 | 0.01 | 0.010 | 0.00 | 0.05 | 0 to 1.17 |

TABLE 12

TM-PCR for gastric fundus

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 16 | 0.02 | 0.022 | 0.00 | 0.15 | 0 to 0.44 |
| T02 | 16 | 0.01 | 0.011 | 0.00 | 0.07 | 0 to 0.26 |

Results: Gastric Ulcer Scores

*H. suis* vaccinated pigs had numerically lower visual analog scores compared to the nonvaccinated pigs, and none of the vaccinated pigs had the most severe Hessing score. Statistically significant differences between groups for either the visual analog scores (Table 13) or the Hessing scores (Table 14) were not observed, however.

TABLE 13

Visual analog gastric ulcer scores

| Treatment | Number of Animals | Ismean | Standard Error | Lower 90% Confidence Limit of Mean | Upper 90% Confidence Limit of mean | Range |
|---|---|---|---|---|---|---|
| T01 | 16 | 22.94 | 6.993 | 11.23 | 34.66 | 0 to 75 |
| T02 | 16 | 19.44 | 6.993 | 7.73 | 31.16 | 0 to 47.6 |

TABLE 14

Hessing gastric ulcer scores

| Treatment | \_\_\_0\_\_\_ | | \_\_\_1\_\_\_ | | \_\_\_2\_\_\_ | | \_\_\_3\_\_\_ | | \_\_\_4\_\_\_ | | Total Observations |
|---|---|---|---|---|---|---|---|---|---|---|---|
| | Number | % | Number | % | Number | % | Number | % | Number | % | Number |
| NTX | 4 | 66.7 | 0 | 0.0 | 1 | 16.7 | 0 | 0.0 | 1 | 16.7 | 6 |
| T01 | 1 | 6.3 | 6 | 37.5 | 4 | 25.0 | 3 | 18.8 | 2 | 12.5 | 16 |
| T02 | 2 | 12.5 | 2 | 12.5 | 9 | 56.3 | 3 | 18.8 | 0 | 0.0 | 16 |

There were no statistically significant differences between groups for scores greater than 0.

Results: Histopathology Scores

There were numerical reductions between the vaccines groups in the visual analog scores of deep and surface lymphoid follicles (Tables 15-16). However, no statistically detectable differences between vaccine groups were observed.

TABLE 15

Deep lymphoid follicle histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 16 | 18.82 | 4.177 | 11.89 | 25.75 | 1.4 to 70.9 |
| T02 | 16 | 12.25 | 3.713 | 6.09 | 18.41 | 1.2 to 71.2 |

TABLE 16

Surface lymphoid follicle histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 16 | 9.80 | 2.949 | 4.91 | 14.69 | 1.5 to 48.2 |
| T02 | 16 | 9.09 | 2.948 | 4.20 | 13.97 | 0.9 to 45.4 |

Conclusions:

The *Helicobacter suis* vaccine reduced colonization of the swine stomach by *H. suis*. The *H. suis* vaccine reduced urease scores compared to saline controls in both the cardia and fundus (P<0.0025 and 0.0199 respectively).

Example 11

Reduction of Candidatus *Helicobacter suis* Colonization by Vaccination of Pigs Using Antigens Obtained from "Candidatus *Helicobacter suis*" Isolates The safety and efficacy of the "Candidatus *Helicobacter suis*" vaccine was determined. The "Candidatus *Helicobacter suis*" antigen was inactivated and disrupted by sonication, followed by sterile filtration and formulation with an oil-in-water emulsion adjuvant. The antigen dose was determined based on the amount of total protein present.

Study Design

Sows were selected as described in the previous Example. All sows were *H. suis* free (Table 17).

TABLE 17

Study Design

| Treatment | Vaccine | N | Regimen | Age at Vaccination[#] | Challenge |
|---|---|---|---|---|---|
| T01 | Saline | 19 | IM | 14, 26, 39 days | 6, 7, 8, 9 wk |
| T02 | *H. suis* | 19 | IM | 14, 26, 39 days | 6, 7, 8, 9 wk |

[#]Intramuscular (IM) injection in the neck, alternately left (day 14), right (day 26), and then left (day 39).
All pigs were euthanized at 16 weeks of age.

TABLE 18

Antigen and IVP Preparation

| IVP* | Antigen Dose | Adjuvant[^] per Dose | Volume per Dose |
|---|---|---|---|
| Saline (PBS) | NA | 1 mL | 2 mL |
| *H. suis* | 500 µg per dose | 1 mL | 2 mL |

*IVP = Investigational Veterinary Product (Vaccine)
[^]The adjuvant- a final concentration of 5% Oil-water emulsion- was mixed 1:1 with the antigen.

Vaccination and Challenge

Pigs were vaccinated by intramuscular injection in the neck at 14, 26 and 39 days of age (Table 18). Control pigs were vaccinated at the same time with an equal volume of saline. Pigs were observed for clinical signs 1 day before and two days after vaccination, and within 1-hour post vaccination. For the *H. suis* challenge, homogenates of scrapings of the upper cell layers and mucus of the antrum of gastric samples which have been tested positive for *H. suis* (using urease test) were used. Viability and dose of the pig stomach homogenate used as challenge material was confirmed as in previous Example.

Post-Challenge Methods and Scoring

Methods and scoring were as described in the previous Example.

Results: Urease

Urease optical density scores were determined for the three (3) major regions of the stomach: antrum, cardia, and fundus. Tables 19-21). There was no statistically significant difference in the urease scores of vaccinated pigs compared to saline controls, though there was a slight numerical reduction in the cardia urease scores.

TABLE 19

Least squares mean gastric antrum urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 85 | 0.63 | 0.235 | 0.17 | 2.40 | 0.04 to 1.8 |
| T02 | 93 | 0.86 | 0.309 | 0.22 | 3.03 | 0.04-1.72 |

Scores with different letters are statistically significantly different from each other (P ≤ 0.10)

TABLE 20

Least squares mean gastric cardia urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 44 | 0.08 | 0.015 | 0.05 | 0.11 | 0.04 to 1.43 |
| T02 | 49 | 0.07 | 0.012 | 0.05 | 0.10 | 0.04 to 0.26 |

Scores with different letters are statistically significantly different from each other (P ≤ 0.10)

TABLE 21

Least squares mean gastric fundus urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 40 | 0.56 | 0.160 | 0.18 | 1.81 | 0.05 to 1.65 |
| T02 | 48 | 0.69 | 0.194 | 0.20 | 2.37 | 0.08 to 1.51 |

Scores with different letters are statistically significantly different from each other (P ≤ 0.10)

Results: PCR

All gastric regional sites were positive for the presence of *H. suis* as determined by qualitative PCR assay except for two animals in T01 cardia and one animal in T02 fundus (Table 22).

TABLE 22

PCR positive/negative score for gastric regional biopsies

| % Positive | Group | |
|---|---|---|
| | T01 | T02 |
| Antrum | 100 | 100 |
| Cardia | 88.9 | 100 |
| Fundus | 100 | 94.1 |

Quantitative PCR for Gastric Regional Biopsies

There was a numerical decrease in the level of *H. suis* DNA in the gastric fundus of vaccinated pigs (Table 25). There were no statistically significant differences for *H. suis* specific TM-PCR conducted on biopsies of gastric antrum, fundus, or cardia between vaccine groups (Tables 23-25).

TABLE 23

TM-PCR for gastric antrum

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 35 | 3.38 | 0.245 | 2.88 | 3.94 | 0 to 4.99 |
| T02 | 34 | 3.85 | 0.199 | 3.45 | 4.29 | 1.55 to 5.34 |

TABLE 24

TM-PCR for gastric cardia

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 18 | 1.77 | 0.341 | 0.40 | 4.50 | 0 to 4.51 |
| T02 | 17 | 1.76 | 0.342 | 0.41 | 4.40 | 0 to 5.28 |

TABLE 25

TM-PCR for gastric fundus

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 18 | 3.37 | 0.362 | 2.63 | 4.27 | 0 to 5.49 |
| T02 | 17 | 2.81 | 0.351 | 2.07 | 3.73 | 0 to 4.66 |

Results: Gastric Ulcer Scores

There were no statistical differences between groups for either the visual analog scores (Table 26) or the Hessing scores (Table 27).

TABLE 26

Visual analog gastric ulcer scores

| Treatment | Number of Animals | lsmean | Standard Error | Lower 90% Confidence Limit of Mean | Upper 90% Confidence Limit of mean | Range |
|---|---|---|---|---|---|---|
| T01 | 18 | 23.89 | 5.300 | 15.04 | 32.74 | 0 to 55.9 |
| T02 | 17 | 33.53 | 6.404 | 22.84 | 44.23 | 0 to 70 |

TABLE 27

Hessing gastric ulcer scores

| Treatment | Score 0 | | Score 1 | | Score 2 | | Score 3 | | Score 4 | | Total Observations |
|---|---|---|---|---|---|---|---|---|---|---|---|
| | Number | % | Number | % | Number | % | Number | % | Number | % | Number |
| T01 | 5 | 27.8 | 0 | 0.0 | 9 | 50.0 | 4 | 22.2 | 0 | 0.0 | 18 |
| T02 | 1 | 5.9 | 2 | 11.8 | 9 | 52.9 | 3 | 17.6 | 2 | 11.8 | 17 |

There were no statistically significant differences between groups for scores greater than 0.

Conclusions:

The *Helicobacter suis* vaccine resulted in a modest reduction in colonization of the swine stomach by *H. suis*.

Example 12

Reduction of Gastric Lesions by Vaccination of Pigs Using "Candidatus *Helicobacter suis*" Vaccines The efficacy of two "Candidatus *Helicobacter suis*" vaccines (different antigen formulations) to reduce gastric lesions was determined. The "Candidatus *Helicobacter suis*" antigen was either disrupted by high-pressure treatment (Avestin) and homogenized with the adjuvant (T02), or was inactivated and disrupted by sonication, followed by sterile filtration and formulation with an oil-in-water emulsion adjuvant (T03). The antigen dose was determined based on the amount of total protein present.

Study Design

Sows were selected from a herd free of "Candidatus *Helicobacter suis*" infection, as determined by PCR and urease screening of stomachs from herdmates at slaughter. Piglets from these sows were allotted to one of three groups: a saline control and two groups receiving "Candidatus *Helicobacter suis*" vaccines (Table 28). An additional group of three pigs was used as a non-treatment control (NTX). The study was a completely randomized design, and each animal was the experimental unit. Following weaning, sows were euthanized and the stomach analyzed by a quantitative urease test and PCR for the presence of *H. suis*. All sows were *H. suis* free.

TABLE 28

Study Design

| Treatment | Vaccine | N | Regimen | Age at Vaccination[#] | Challenge |
|---|---|---|---|---|---|
| T01 | Saline | 15 | IM | 8, 22, 36 days | 40, 47, 54, 61 days |
| T02 | H. suis Avestin | 15 | IM | 8, 22, 36 days | 40, 47, 54, 61 days |
| T03 | H. suis Sonicate | 15 | IM | 8, 22, 36 days | 40, 47, 54, 61 days |
| NTX | None | 3 | None | None | None |

[#]Intramuscular (IM) injection in the neck, alternately left (8 days), right (22 days), and then left (36 days).
All pigs were euthanized at 14 weeks of age.

TABLE 29

Antigen and IVP Preparation

| IVP* | Antigen Dose | Adjuvant^ per Dose | Volume per Dose |
|---|---|---|---|
| Saline (PBS) | NA | 1 mL | 2 mL |
| H. suis Avestin | 500 µg per dose | 1 mL | 2 mL |
| H. suis Sonicate | 500 µg per dose | 1 mL | 2 mL |

*IVP = Investigational Veterinary Product (Vaccine)
^The adjuvant- a final concentration of 5% Oil-water emulsions- was be mixed 1:1 with the antigen.

Vaccination and Challenge

Pigs were vaccinated by intramuscular injection in the neck at 8, 22 and 36 days of age (Table 29). Control pigs were vaccinated at the same time with an equal volume of saline. Pigs were observed for clinical signs 1 day before and two days after vaccination, and within 1-hour post vaccination. For the *H. suis* challenge, homogenates of scrapings of the upper cell layers and mucus of the antrum of gastric samples which have been tested positive for *H. suis* (using urease test) were used. Viability and dose of the pig stomach homogenate used as challenge material was confirmed as in previous Examples.

In addition, the challenge also contained in vitro grown *H. suis*. For preparation of in vitro grown challenge material, *H. suis* was grown on a 10% sheep blood *Brucella* agar plate supplemented with Skirrows and Vitox and Amphotericin B at 37° C. and 10% $CO_2$ for 4 days. The organism was passaged in this way to achieve approximately $1 \times 10^8$ CFU per plate. The pigs were challenged with this culture at a dose of $1 \times 10^9$ CFU per pig per dose. This material was tested for viability as described above.

Post-Challenge Methods and Scoring

Methods and scoring were as described in the previous two Examples. In addition, for histopathological examination, gastric mucosal tissue samples are fixed in 10% phosphate buffered formalin, processed by routine methods, and embedded in paraffin. One 5-µm section is immunohistochemically stained with a polyclonal goat anti-*H. pylori* antibody (Dakocytomation, Denmark A/S: Glostrup, Denmark) as described by De Groote et al. (2000). A second section is stained with HE for scoring of gastritis. Histopathological changes are scored for 1) Diffuse lymphocytes—a score for the diffuse infiltration of lymphocytes in the propria mucosae; 2) Formation of lymphoid follicles in the propria mucosae; 3) Formation of lymphoid follicles under the surface epithelium; 4) Diffuse infiltration of plasma cells in the propria mucosae. The presence of lymphoid follicles under the surface epithelium and the infiltration of plasma cells are very noteworthy and characteristic lesions. These were scored by severity with a score of 0-3. 1=mild, 2=moderate, and 3=severe. They were also scored using a visual analog scale (0-100 mm).

Results: Urease

Urease optical density scores were determined for the three (3) major regions of the stomach: antrum, cardia, and fundus (Tables 30-32). There was no statistically significant difference in the urease scores of vaccinated pigs compared to saline controls.

TABLE 30

Least squares mean gastric antrum urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 80 | 0.91 | 0.226 | 0.60 | 1.38 | 0.07 to 1.97 |
| T02 | 79 | 1.04 | 0.259 | 0.68 | 1.58 | 0.06 to 2.03 |
| T03 | 80 | 0.97 | 0.241 | 0.64 | 1.47 | 0.06 to 1.83 |

Scores with different letters are statistically significantly different from each other ($P \leq 0.10$)

TABLE 31

Least squares mean gastric cardia urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 44 | 0.06 | 0.005 | 0.05 | 0.07 | 0.04 to 0.11 |
| T02 | 45 | 0.09 | 0.009 | 0.07 | 0.11 | 0.04 to 0.22 |
| T03 | 45 | 0.07 | 0.006 | 0.06 | 0.08 | 0.05 to 0.2 |

Scores with different letters are statistically significantly different from each other ($P \leq 0.10$)

TABLE 32

Least squares mean gastric fundus urease scores

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 44 | 0.15 | 0.027 | 0.10 | 0.21 | 0.05 to 1.63 |
| T02 | 42 | 0.23 | 0.042 | 0.16 | 0.32 | 0.05 to 2.57 |
| T03 | 41 | 0.14 | 0.026 | 0.10 | 0.20 | 0.03 to 1.02 |

Scores with different letters are statistically significantly different from each other ($P \leq 0.10$)

Results: PCR

Vaccinated pigs tended to be less likely to have detectable *H. suis* DNA in the fundus of the stomach. This reduction was numerical, but was not statistically significant, given the number of pigs in this study. The percentage of gastric regional sites of challenged pigs positive for the presence of *H. suis* is noted below. All NTX gastric biopsies were negative (Table 33).

TABLE 33

PCR positive/negative score for gastric regional biopsies

| | Group | | | |
|---|---|---|---|---|
| | NTX | T01 | T02 | T03 |
| | | N | | |
| % Positive | 3 | 15 | 15 | 15 |
| Antrum | 0 | 93.3 | 93.3 | 86.7 |
| Cardia | 0 | 6.7 | 13.3 | 13.3 |
| Fundus | 0 | 40 | 40 | 20 |

Quantitative PCR for Gastric Mucosal Scrapings

There were no statistically significant differences for TM-PCR for gastric scrapings between vaccine groups (Tables 34-35), indicating that there was no detectable difference in the level of *Helicobacter* DNA in gastric scrapings between vaccine groups. The discrepancy between this assay and the results in Tables 13-15 (where the vaccines reduced the number of positive pigs) may reflect the relative difference sensitivities in these assays or in the variability of sample collection between small biopsies and scrapings of large areas of gastric mucosa.

TABLE 34

TM-PCR for gastric scraping (*H.* spp DNA)

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 14 | 8.71 | 0.221 | 8.35 | 9.10 | 7.14 to 9.73 |
| T02 | 15 | 8.98 | 0.220 | 8.62 | 9.36 | 7.5 to 10.16 |
| T03 | 15 | 8.89 | 0.218 | 8.53 | 9.26 | 7.01 to 9.94 |

TABLE 35

TM-PCR for gastric scraping (*H. suis* DNA)

| Treatment | Number of Observations | Geometric Least Squares Mean | Standard Error | Lower 90% Confidence Limit of Mean | Upper 90% Confidence Limit of Mean | Range |
|---|---|---|---|---|---|---|
| T01 | 14 | 6.91 | 0.204 | 6.57 | 7.26 | 5.42 to 7.9 |
| T02 | 15 | 7.45 | 0.213 | 7.10 | 7.82 | 5.55 to 8.56 |
| T03 | 15 | 7.20 | 0.206 | 6.86 | 7.55 | 5.61 to 8.6 |

Results: Gastric Ulcer Scores

*H. suis* vaccinated pigs (T03) had numerically lower visual analog scores compared to the nonvaccinated pigs (Table 36). Both vaccines (T02 and T03) tended to reduce the number of pigs with gastric lesions (as measured by Hessing scores) (Table 37), and there was a statistically significant reduction of the number of pigs with gastric lesions in the T03 pigs, i.e., significantly more vaccinated pigs were free of gastric lesions than the non-vaccinated pigs.

TABLE 36

Visual analog gastric ulcer scores

| Treatment | Number of Animals | Ismean | Standard Error | Lower 90% Confidence Limit of Mean | Upper 90% Confidence Limit of mean | Range |
|---|---|---|---|---|---|---|
| T01 | 15 | 35.93 | 6.986 | 24.17 | 47.70 | 9 to 80 |
| T02 | 15 | 34.40 | 6.986 | 22.64 | 46.16 | 0 to 83 |
| T03 | 15 | 22.87 | 6.986 | 11.10 | 34.63 | 0 to 78 |

TABLE 37

Hessing gastric ulcer scores

| treatment | Score 0 | | Score 1 | | Score 2 | | Score 3 | | Score 4 | | Score 5 | | total observations |
|---|---|---|---|---|---|---|---|---|---|---|---|---|---|
| | N | % | N | % | N | % | N | % | N | % | N | % | N |
| T01 | 0 | 0.0[a] | 6 | 40.0 | 4 | 26.7 | 1 | 6.7 | 1 | 6.7 | 3 | 20.0 | 15 |
| T02 | 2 | 13.3[a] | 2 | 13.3 | 7 | 46.7 | 0 | 0.0 | 2 | 13.3 | 2 | 13.3 | 15 |
| T03 | 4 | 26.7[b] | 4 | 26.7 | 5 | 33.3 | 0 | 0.0 | 0 | 0.0 | 2 | 13.3 | 15 |

T03 vaccinated pigs had statistically significantly fewer pigs (P < 0.1) with Hessing scores greater than 0.

Results: Histopathology Scores

Vaccinated pigs (T03) tended to have fewer surface lymphoid follicles than non-vaccinated pigs. There were, however, no statistically significant differences between vaccine groups for visual analog scores of deep and surface lymphoid follicles nor of other histological scores (Tables 38-43).

TABLE 38

Deep lymphoid follicle, Antrum, histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 30 | 37.27 | 6.764 | 26.02 | 48.52 | 0 to 79 |
| T02 | 30 | 44.17 | 6.764 | 32.92 | 55.42 | 0 to 88 |
| T03 | 30 | 32.73 | 6.764 | 21.48 | 43.98 | 1 to 85 |

TABLE 39

Deep lymphoid follicle, Cardia, histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 15 | 20.27 | 3.426 | 14.50 | 26.04 | 0 to 51 |
| T02 | 15 | 31.73 | 6.052 | 21.54 | 41.92 | 1 to 68 |
| T03 | 15 | 25.67 | 5.019 | 17.22 | 34.12 | 0 to 57 |

TABLE 40

Deep lymphoid follicle, Fundus, histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 15 | 10.80 | 5.644 | 1.30 | 20.30 | 0 to 71 |
| T02 | 15 | 5.93 | 2.140 | 2.33 | 9.54 | 0 to 26 |
| T03 | 15 | 14.67 | 3.338 | 9.05 | 20.29 | 1 to 41 |

TABLE 41

Surface lymphoid follicle, Antrum, histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 30 | 24.07 | 4.459 | 16.65 | 31.48 | 0 to 70 |
| T02 | 30 | 30.23 | 4.459 | 22.82 | 37.65 | 0 to 77 |
| T03 | 30 | 18.90 | 4.459 | 11.48 | 26.32 | 0 to 59 |

TABLE 42

Surface lymphoid follicle, Cardia, histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 15 | 6.93 | 2.511 | 2.71 | 11.16 | 0 to 24 |
| T02 | 15 | 9.53 | 2.511 | 5.31 | 13.76 | 0 to 36 |
| T03 | 15 | 6.40 | 2.511 | 2.17 | 10.63 | 0 to 25 |

TABLE 43

Surface lymphoid follicle, Fundus, histopathological visual analog scores

| Treatment | Number of Animals | Ismean | Standard Error | Lower 90% Confidence Limit of Mean | Upper 90% Confidence Limit of Mean | Range |
|---|---|---|---|---|---|---|
| T01 | 15 | 3.40 | 2.356 | −0.57 | 7.37 | 0 to 35 |
| T02 | 15 | 0.60 | 0.466 | −0.18 | 1.38 | 0 to 7 |
| T03 | 15 | 1.53 | 1.073 | −0.27 | 3.34 | 0 to 16 |

Conclusions:

The sonicated *Helicobacter suis* vaccine (T03) significantly reduced the number of pigs with gastric lesions. There was, however, no observed reduction of colonization in this study.

The vaccines may be modifying the immune response to the infection in order to reduce the pathological effect of the infection. This is consistent with the observation that vaccinated pigs also tended to have had fewer surface lymphoid follicles in their gastric mucosa following challenge.

All publications and patent applications mentioned in this specification are herein incorporated by reference to the same extent as if each independent publication or patent application was specifically and individually indicated to be incorporated by reference.

Other embodiments are within the scope of the claims.

What is claimed is:

1. A Candidatus *Helicobacter suis* isolate free from other bacteria or fungi present in the stomach, obtainable by a method which comprises the steps of cultivating a sample in a cultivation system, said system comprising a cultivation medium having a pH between 5.0 and 6.0, wherein said medium is supplemented with at least 10% serum or at least 7.5% blood and wherein said isolate is deposited as LMG P-24758.

2. A method of treating an animal for a Candidatus *Helicobacter suis* infection comprising administering to said animal a Candidatus *Helicobacter suis* isolate antigen preparation free from other bacteria or fungi present in the stomach, wherein said isolate is deposited as LMG P-24758.

3. A Candidatus *Helicobacter suis* isolate free from other bacteria or fungi present in a stomach, wherein said isolate is deposited as LMG P-24758.

* * * * *

UNITED STATES PATENT AND TRADEMARK OFFICE
CERTIFICATE OF CORRECTION

PATENT NO. : 7,939,079 B2
APPLICATION NO. : 12/463300
DATED : May 10, 2011
INVENTOR(S) : Baele et al.

It is certified that error appears in the above-identified patent and that said Letters Patent is hereby corrected as shown below:

Column 10, Line 56, replace "antigentic" with --antigenic--.

Column 15, Lines 19-20, replace "curvature major" with --*curvatura major*--.

Column 23, Line 54, replace "(Temmier Pharma)" with --(Temmler Pharma)--.

Signed and Sealed this
Fourth Day of December, 2012

David J. Kappos
*Director of the United States Patent and Trademark Office*